United States Patent [19]

Choo et al.

[11] Patent Number: 6,013,453
[45] Date of Patent: Jan. 11, 2000

[54] BINDING PROTEINS FOR RECOGNITION OF DNA

[75] Inventors: Yen Choo, Singapore, Singapore; Aaron Klug, Cambridge, United Kingdom; Isidro Sanchez Garcia, Salamanca, Spain

[73] Assignee: Medical Research Council, London, United Kingdom

[21] Appl. No.: 09/139,762

[22] Filed: Aug. 25, 1998

Related U.S. Application Data

[63] Continuation of application No. 08/793,408, filed as application No. PCT/GB95/01949, Aug. 17, 1995.

[30] Foreign Application Priority Data

Aug. 20, 1994 [GB] United Kingdom .................. 9416880
Nov. 8, 1994 [GB] United Kingdom .................. 9422534
Jul. 19, 1995 [GB] United Kingdom .................. 9514698

[51] Int. Cl.$^7$ ............................ C12Q 1/68; C07H 21/04
[52] U.S. Cl. ................................................ 435/6; 536/23.4
[58] Field of Search ................................ 435/6; 536/23.4

[56] References Cited

U.S. PATENT DOCUMENTS 5,498,530 3/1996 Schatz et al. .......................... 435/69.1

OTHER PUBLICATIONS

Rebar et al: "Zinc Finger Phage: Affinity Selection of Fingers with New DNA–Binding Specificites", Science, vol. 263, Feb. 4, 1994, pp. 671–673.
Jamieson et al: "In Vitro Selection of Zinc with Altered DNA–Binding Specificity", Biochemistry, 1994, 33, pga 5689–5695.
Thiesen et al: "Dtermination of DNA binding specificities of mutated zinc finger domains", FEBS Letters, vol. 283, No. 1, May 1991, pp. 23–26.
Jacobs: "Determination of the base recognition positions of zinc fingers from sequence analysis", The EMBO Journal, vol. 11, No. 12, 1992, pp. 4507–4517.
Desjarlais et al: "Toward rules relating zinc finger protein sequences and DNA binding site preferences" Proc.Natl.Acad.Sci.USA, vol. 89, Aug. 1992, Biophysics, pp. 7345–7349.

Nardelli et al: "Zinc finger–DNA recognition: analysis of base specificity by site—directed mutagenesis", Nucleic Acids Research, vol. 20, No. 16, pp. 4137–4144.
Desjarlais et al: "Use of a zinc–finger consensus sequence framework and specificity rules to design specific DNA binding proteins", Proc.Natl.Acad.Sci.USA, vol. 90, Mar. 1993, Biochemistry, pp. 2256–2260.
Choo et al: "Toward a code for the interactions of zinc fingers with DNA: Selection of randomized fingers displayed on phage", Proc.Natl.Acad.Sci.USA, vol. 91, Nov. 1994, Biochemistry, pp. 11163–11167.
Choo et al: "Selection of DNA binding sites for zinc fingers using rationally randomized DNA reveals coded interactions", Proc.Natl.Acad.Sci.USA, vol. 91, Nov. 1994, Biochemistry, pp. 11168–11172.
Choo et al: "In Vivo repression by a site–specific DNA–binding protein designed against an oncogenic sequence", Nature, vol. 372, Dec. 15, 1994, pp. 642–645.
Wu et al: "Building zinc fingers by selection: Toward a therapeutic application", Proc.Natl.Acad.Sci.USA, vol. 92, Jan. 1995, Biochemistry, pp. 344–348.
Klug et al: "Zinc Fingers", The FASEB Journal, May 1995, vol. 9, No. 8, pp. 597–604.
Choo et al: "Designing DNA–binding proteins on the surface of filamentous phage", Current Opinion in Biotechnology, 1995, 6: pp. 431–436.
Orkin, Report and recommendation of the panel to assess the NIH investment in research on gene therapy, Dec. 7, 1995.
Freisen et al. Phage display of RNA binding zinc fingers from transcription factor IIIA., J. Biol. Chem. vol. 272(17): 10994–10997, Apr. 25, 1997.
Blaese et al., Vectors in cancer therapy: how will they deliver?, Cancer Gene Therapy, vol. 2(4): 291–297, Oct. 1995.

*Primary Examiner*—Nancy Degen
*Assistant Examiner*—William Sandals
*Attorney, Agent, or Firm*—Pillsbury Madison & Sutro LLP

[57] ABSTRACT

Disclosed are libraries of DNA sequences encoding zinc finger binding motifs for display on a particle, together with methods of designing zinc finger binding polypeptides for binding to a particular target sequence and, inter alia, use of designed zinc finger polypeptides for various in vitro or in vivo applications.

26 Claims, 14 Drawing Sheets

| | | | | | | | | | | |
|---|---|---|---|---|---|---|---|---|---|---|
| 1 | BCR - ABL | | | TTC | CAT | GGA | GAC | GCA | G | AA | GCC | CTT | CAG | CGG | CCA |
| 2 | BCR | | | TTC | CAT | GGA | GAC | GCA | G | gt | gag | ttc | ctc | acg | cca |
| 3 | ABL | ccc | ctt | tct | ctt | cca | g | AA | GCC | CTT | CAG | CGG | CCA |

Fig.6

|    |   |   |   |   |   |   |   |   |   |   |   |   |   |   | -1 | 1 | 2 | 3 | 4 | 5 | 6 | 7 | 8 | 9 |   |   |   |   |   |
|----|---|---|---|---|---|---|---|---|---|---|---|---|---|---|----|---|---|---|---|---|---|---|---|---|---|---|---|---|---|
| 1A | M | A | E | E | K | P | F | Q | C | R | I | C | M | R | N  | F | S | D | R | S | S | L | T | R | H | H | T | R | H | T G E K P |
| 1B | M | A | E | E | K | P | F | Q | C | R | I | C | M | R | N  | F | S | E | R | G | T | L | A | R | H | E | K | H | H | T G E K P |
| 2A |   |   |   |   |   |   | F | Q | C | R | I | C | M | R | N  | F | S | Q | G | G | N | L | V | R | H | L | R | H | H | T G E K P |
| 3A |   |   |   |   |   |   | F | Q | C | R | I | C | M | R | N  | F | S | Q | A | Q | T | L | Q | R | H | L | K | H | H | T G E K |
| 3B |   |   |   |   |   |   | F | Q | C | R | I | C | M | R | N  | F | S | Q | A | A | T | L | Q | R | H | L | K | H | H | T G E K |
| 3C |   |   |   |   |   |   | F | Q | C | R | I | C | M | R | N  | F | S | Q | A | Q | D | L | Q | R | H | L | K | H | H | T G E K |

β-SHEET     β-SHEET     α-HELIX     LINKER

Fig. 7

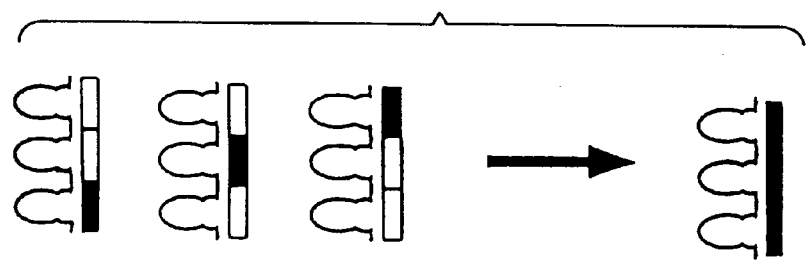
Fig. IOC
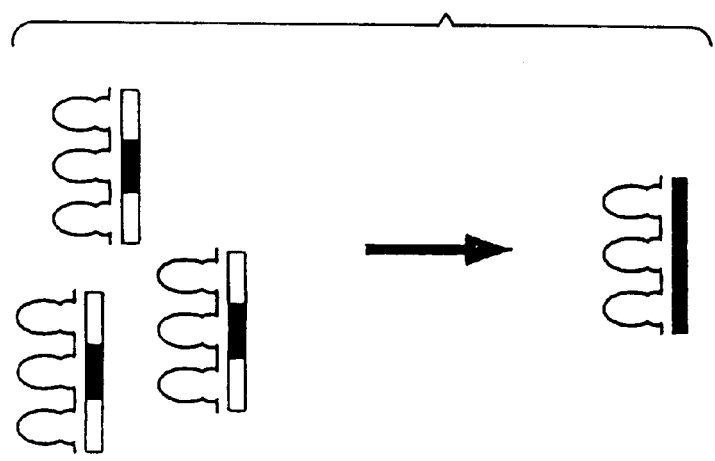
Fig. IOB
Fig. IOA

SEQUENCE LISTING (1) GENERAL INFORMATION:

(iii) NUMBER OF SEQUENCES: 125

(2) INFORMATION FOR SEQ ID NO: 1:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (xi) SEQUENCE DESCRIPTION: SEQ ID NO: 1:

CTCCTGCAGT TGGACCTGTG CCATGGCCGG CTGGGCCGCA TAGAATGGAA           50

CAACTAAAGC                                                      60

(2) INFORMATION FOR SEQ ID NO: 2:

(i) SEQUENCE CHARACTERISTICS:
            (A) LENGTH: 92 amino acids
            (B) TYPE: amino acid
            (C) STRANDEDNESS:
            (D) TOPOLOGY: unknown (ii) MOLECULE TYPE: protein (xi) SEQUENCE DESCRIPTION: SEQ ID NO: 2:

Met Ala Glu Glu Arg Pro Tyr Ala Cys Pro
                 5                  10

Val Glu Ser Cys Asp Arg Arg Phe Ser Arg
                15                  20

Ser Asp Glu Leu Thr Arg His Ile Arg Ile
                25                  30

His Thr Gly Gln Lys Pro Phe Gln Cys Arg
                35                  40

Ile Cys Met Arg Asn Phe Ser Xaa Xaa Xaa
                45                  50

Xaa Leu Xaa Xaa His Xaa Arg Thr His Thr
                55                  60

Gly Glu Lys Pro Phe Ala Cys Asp Ile Cys
                65                  70

Gly Arg Lys Phe Ala Arg Ser Asp Glu Arg
                75                  80

Lys Arg His Thr Lys Ile His Leu Arg Gln
                85                  90

Lys Asp (2) INFORMATION FOR SEQ ID NO: 3:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (xi) SEQUENCE DESCRIPTION: SEQ ID NO: 3:

TATGACTTGG ATGGGAGACC GCCTGG                                    26

(2) INFORMATION FOR SEQ ID NO: 4:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (xi) SEQUENCE DESCRIPTION: SEQ ID NO: 4:

AATTCCAGGC GGTCTCCCAT CCAAGTCA                                  28

(2) INFORMATION FOR SEQ ID NO: 5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 5:

TATATAGCGT GGGCGTATAT A                                    21

(2) INFORMATION FOR SEQ ID NO: 6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 6:

GCGTATATAC GCCCACGCTA TATA                                24

(2) INFORMATION FOR SEQ ID NO: 7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 7:

TATATAGCGN NNGCGTATAT A                                    21

(2) INFORMATION FOR SEQ ID NO: 8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 8:

GCGTATATAC GCNNNCGCTA TATA                                24

(2) INFORMATION FOR SEQ ID NO: 9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 9:

TTCCATGGAG ACGCAGAAGC CCTTCAGCGG CCA                          33

(2) INFORMATION FOR SEQ ID NO: 10:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 10:

TTCCATGGAG ACGCAGGTGA GTTCCTCACG CCA                          33

-continued

```
(2) INFORMATION FOR SEQ ID NO: 11:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 11:

CCCCTTTCTC TTCCAGAAGC CCTTCAGCGG CCA                                    33

(2) INFORMATION FOR SEQ ID NO: 12:

(i) SEQUENCE CHARACTERISTICS:
        (A) LENGTH: 33 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 12:

Met Ala Glu Glu Lys Pro Phe Gln Cys Arg
                 5                  10

Ile Cys Met Arg Asn Phe Ser Asp Arg Ser
                15                  20

Ser Leu Thr Arg His Thr Arg His Thr Gly
                25                  30

Glu Lys Pro (2) INFORMATION FOR SEQ ID NO: 13:

(i) SEQUENCE CHARACTERISTICS:
        (A) LENGTH: 33 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 13:

Met Ala Glu Glu Lys Pro Phe Gln Cys Arg
                 5                  10

Ile Cys Met Arg Asn Phe Ser Glu Arg Gly
                15                  20

Thr Leu Ala Arg His Glu Lys His Thr Gly
                25                  30

Glu Lys Pro (2) INFORMATION FOR SEQ ID NO: 14:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 14:

Phe Gln Cys Arg Ile Cys Met Arg Asn Phe
                 5                  10

Ser Gln Gly Gly Asn Leu Val Arg His Leu
                15                  20

Arg His Thr Gly Glu Lys Pro
```

25

(2) INFORMATION FOR SEQ ID NO: 15:

(i) SEQUENCE CHARACTERISTICS:
        (A) LENGTH: 26 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 15:

Phe Gln Cys Arg Ile Cys Met Arg Asn Phe
                5                   10

Ser Gln Ala Gln Thr Leu Gln Arg His Leu
            15                  20

Lys His Thr Gly Glu Lys
            25

(2) INFORMATION FOR SEQ ID NO: 16:

(i) SEQUENCE CHARACTERISTICS:
        (A) LENGTH: 26 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 16:

Phe Gln Cys Arg Ile Cys Met Arg Asn Phe
                5                   10

Ser Gln Ala Ala Thr Leu Gln Arg His Leu
            15                  20

Lys His Thr Gly Glu Lys
            25

(2) INFORMATION FOR SEQ ID NO: 17:

(i) SEQUENCE CHARACTERISTICS:
        (A) LENGTH: 26 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 17:

Phe Gln Cys Arg Ile Cys Met Arg Asn Phe
                5                   10

Ser Gln Ala Gln Asp Leu Gln Arg His Leu
            15                  20

Lys His Thr Gly Glu Lys
            25

(2) INFORMATION FOR SEQ ID NO: 18:

(i) SEQUENCE CHARACTERISTICS:
        (A) LENGTH: 89 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO: 18:

```
Met Ala Glu Glu Lys Pro Phe Gln Cys Arg
                 5                  10

Ile Cys Met Arg Asn Phe Ser Asp Arg Ser
                15                  20

Ser Leu Thr Arg His Thr Arg Thr His Thr
                25                  30

Gly Glu Lys Pro Phe Gln Cys Arg Ile Cys
                35                  40

Met Arg Asn Phe Ser Asp Arg Ser His Leu
                45                  50

Thr Arg His Thr Arg Thr His Thr Gly Glu
                55                  60

Lys Pro Phe Gln Cys Arg Ile Cys Met Arg
                65                  70

Asn Phe Ser Asp Arg Ser Asn Leu Thr Arg
                75                  80

His Thr Arg Thr His Thr Gly Glu Lys
                85

(2) INFORMATION FOR SEQ ID NO: 19:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 19:

Arg Ser Asp His Leu Thr Thr His Ile Arg
                 5                  10

(2) INFORMATION FOR SEQ ID NO: 20:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 20:

Arg Val Asp Ala Leu Glu Ala His Arg Arg
                 5                  10

(2) INFORMATION FOR SEQ ID NO: 21:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 21:

Gln Arg Ala Ser Leu Ala Ser His Met Arg
                 5                  10

(2) INFORMATION FOR SEQ ID NO: 22:

(i) SEQUENCE CHARACTERISTICS:
```

(A) LENGTH: 10 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO: 22:

Asn Arg Asp Thr Leu Thr Arg His Ser Lys
                 5                  10

(2) INFORMATION FOR SEQ ID NO: 23:

(i) SEQUENCE CHARACTERISTICS:
            (A) LENGTH: 10 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO: 23:

Gln Lys Gly His Leu Thr Glu His Arg Lys
                 5                  10

(2) INFORMATION FOR SEQ ID NO: 24:

(i) SEQUENCE CHARACTERISTICS:
            (A) LENGTH: 10 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO: 24:

Gln Ser Val His Leu Gln Ser His Ser Arg
                 5                  10

(2) INFORMATION FOR SEQ ID NO: 25:

(i) SEQUENCE CHARACTERISTICS:
            (A) LENGTH: 10 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO: 25:

Arg Leu Asp Gly Leu Arg Thr His Leu Lys
                 5                  10

(2) INFORMATION FOR SEQ ID NO: 26:

(i) SEQUENCE CHARACTERISTICS:
            (A) LENGTH: 10 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO: 26:

Thr Pro Gly Asn Leu Thr Arg His Gly Arg
                 5                  10

(2) INFORMATION FOR SEQ ID NO: 27:

(i) SEQUENCE CHARACTERISTICS:

(A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 27:

Asn Gly Gly Asn Leu Gly Arg His Met Lys
                  5                  10

(2) INFORMATION FOR SEQ ID NO: 28:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 28:

Arg Ala Asp Ala Leu Met Val His Lys Arg
                  5                  10

(2) INFORMATION FOR SEQ ID NO: 29:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 29:

Asn Gln Ser Asn Leu Glu Arg His His Arg
                  5                  10

(2) INFORMATION FOR SEQ ID NO: 30:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 30:

Asp Arg Ser Asn Leu Glu Arg His Thr Arg
                  5                  10

(2) INFORMATION FOR SEQ ID NO: 31:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 31:

Arg Ser Asp Thr Leu Lys Lys His Gly Lys
                  5                  10

(2) INFORMATION FOR SEQ ID NO: 32:

(i) SEQUENCE CHARACTERISTICS:

```
            (A) LENGTH: 10 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO: 32:

Gln Gln Ser Asn Leu Val Arg His Gln Arg
                 5                  10

(2) INFORMATION FOR SEQ ID NO: 33:

(i) SEQUENCE CHARACTERISTICS:
            (A) LENGTH: 10 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO: 33:

Asn Gly Ala Asn Leu Glu Arg His Arg Arg
                 5                  10

(2) INFORMATION FOR SEQ ID NO: 34:

(i) SEQUENCE CHARACTERISTICS:
            (A) LENGTH: 10 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO: 34:

Arg Glu Asp Ala Leu Thr Ser His Glu Arg
                 5                  10

(2) INFORMATION FOR SEQ ID NO: 35:

(i) SEQUENCE CHARACTERISTICS:
            (A) LENGTH: 10 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO: 35:

Arg Gly Asp His Leu Lys Asp His Ile Lys
                 5                  10

(2) INFORMATION FOR SEQ ID NO: 36:

(i) SEQUENCE CHARACTERISTICS:
            (A) LENGTH: 10 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO: 36:

Arg Gly Pro Asp Leu Ala Arg His Gly Arg
                 5                  10

(2) INFORMATION FOR SEQ ID NO: 37:

(i) SEQUENCE CHARACTERISTICS:
```

(A) LENGTH: 10 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO: 37:

Arg Glu Asp Val Leu Ile Arg His Gly Lys
                 5                  10

(2) INFORMATION FOR SEQ ID NO: 38:

(i) SEQUENCE CHARACTERISTICS:
            (A) LENGTH: 10 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO: 38:

Arg Ser Asp Leu Leu Gln Arg His His Lys
                 5                  10

(2) INFORMATION FOR SEQ ID NO: 39:

(i) SEQUENCE CHARACTERISTICS:
            (A) LENGTH: 10 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO: 39:

Arg Gln Asp Thr Leu Val Gly His Glu Arg
                 5                  10

(2) INFORMATION FOR SEQ ID NO: 40:

(i) SEQUENCE CHARACTERISTICS:
            (A) LENGTH: 10 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO: 40:

Arg Ala Ala Asp Leu Asn Arg His Val Arg
                 5                  10

(2) INFORMATION FOR SEQ ID NO: 41:

(i) SEQUENCE CHARACTERISTICS:
            (A) LENGTH: 10 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO: 41:

Ser Gln Gly Asn Leu Gln Arg His Gly Arg
                 5                  10

(2) INFORMATION FOR SEQ ID NO: 42:

(i) SEQUENCE CHARACTERISTICS:

(A) LENGTH: 10 amino acids
          (B) TYPE: amino acid
          (C) STRANDEDNESS:
          (D) TOPOLOGY: unknown (ii) MOLECULE TYPE: peptide (xi) SEQUENCE DESCRIPTION: SEQ ID NO: 42:

Thr Gly Gly Ser Leu Ala Arg His Glu Arg
                 5                  10

(2) INFORMATION FOR SEQ ID NO: 43:

(i) SEQUENCE CHARACTERISTICS:
          (A) LENGTH: 10 amino acids
          (B) TYPE: amino acid
          (C) STRANDEDNESS:
          (D) TOPOLOGY: unknown (ii) MOLECULE TYPE: peptide (xi) SEQUENCE DESCRIPTION: SEQ ID NO: 43:

Asp His Ala Asn Leu Ala Arg His Thr Arg
                 5                  10

(2) INFORMATION FOR SEQ ID NO: 44:

(i) SEQUENCE CHARACTERISTICS:
          (A) LENGTH: 10 amino acids
          (B) TYPE: amino acid
          (C) STRANDEDNESS:
          (D) TOPOLOGY: unknown (ii) MOLECULE TYPE: peptide (xi) SEQUENCE DESCRIPTION: SEQ ID NO: 44:

Leu Gln Ser Asn Leu Val Arg His Gln Arg
                 5                  10

(2) INFORMATION FOR SEQ ID NO: 45:

(i) SEQUENCE CHARACTERISTICS:
          (A) LENGTH: 10 amino acids
          (B) TYPE: amino acid
          (C) STRANDEDNESS:
          (D) TOPOLOGY: unknown (ii) MOLECULE TYPE: peptide (xi) SEQUENCE DESCRIPTION: SEQ ID NO: 45:

Arg Lys Asp Val Leu Val Ser His Val Arg
                 5                  10

(2) INFORMATION FOR SEQ ID NO: 46:

(i) SEQUENCE CHARACTERISTICS:
          (A) LENGTH: 10 amino acids
          (B) TYPE: amino acid
          (C) STRANDEDNESS:
          (D) TOPOLOGY: unknown (ii) MOLECULE TYPE: peptide (xi) SEQUENCE DESCRIPTION: SEQ ID NO: 46:

Arg Arg Asp Val Leu Met Asn His Ile Arg
                 5                  10

(2) INFORMATION FOR SEQ ID NO: 47:

(i) SEQUENCE CHARACTERISTICS:

(A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 47:

Gln Gly Gly Asn Leu Val Arg His Leu Arg
                 5                  10

(2) INFORMATION FOR SEQ ID NO: 48:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 48:

Ser Arg Asp Val Leu Arg Arg His Asn Arg
                 5                  10

(2) INFORMATION FOR SEQ ID NO: 49:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 49:

Glu Lys Ala Thr Leu Ala Arg His Met Lys
                 5                  10

(2) INFORMATION FOR SEQ ID NO: 50:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 50:

Gln Ala Gln Thr Leu Gln Arg His Leu Lys
                 5                  10

(2) INFORMATION FOR SEQ ID NO: 51:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 51:

Ile Ala Ser Asn Leu Leu Arg His Gln Arg
                 5                  10

(2) INFORMATION FOR SEQ ID NO: 52:

(i) SEQUENCE CHARACTERISTICS:

(A) LENGTH: 10 amino acids
       (B) TYPE: amino acid
       (C) STRANDEDNESS:
       (D) TOPOLOGY: unknown (ii) MOLECULE TYPE: peptide (xi) SEQUENCE DESCRIPTION: SEQ ID NO: 52:

Arg Gly Asp His Leu Lys Asp His Ile Lys
             5                  10

(2) INFORMATION FOR SEQ ID NO: 53:

(i) SEQUENCE CHARACTERISTICS:
       (A) LENGTH: 10 amino acids
       (B) TYPE: amino acid
       (C) STRANDEDNESS:
       (D) TOPOLOGY: unknown (ii) MOLECULE TYPE: peptide (xi) SEQUENCE DESCRIPTION: SEQ ID NO: 53:

Arg Ser Asp His Leu Thr Thr His Ile Arg
             5                  10

(2) INFORMATION FOR SEQ ID NO: 54:

(i) SEQUENCE CHARACTERISTICS:
       (A) LENGTH: 10 amino acids
       (B) TYPE: amino acid
       (C) STRANDEDNESS:
       (D) TOPOLOGY: unknown (ii) MOLECULE TYPE: peptide (xi) SEQUENCE DESCRIPTION: SEQ ID NO: 54:

Gln Leu Ala His Leu Ser Thr His Lys Arg
             5                  10

(2) INFORMATION FOR SEQ ID NO: 55:

(i) SEQUENCE CHARACTERISTICS:
       (A) LENGTH: 10 amino acids
       (B) TYPE: amino acid
       (C) STRANDEDNESS:
       (D) TOPOLOGY: unknown (ii) MOLECULE TYPE: peptide (xi) SEQUENCE DESCRIPTION: SEQ ID NO: 55:

Gln Ser Val His Leu Gln Ser His Ser Arg
             5                  10

(2) INFORMATION FOR SEQ ID NO: 56:

(i) SEQUENCE CHARACTERISTICS:
       (A) LENGTH: 10 amino acids
       (B) TYPE: amino acid
       (C) STRANDEDNESS:
       (D) TOPOLOGY: unknown (ii) MOLECULE TYPE: peptide (xi) SEQUENCE DESCRIPTION: SEQ ID NO: 56:

Gln Lys Gly His Leu Thr Glu His Arg Lys
             5                  10

(2) INFORMATION FOR SEQ ID NO: 57:

(i) SEQUENCE CHARACTERISTICS:

```
           (A) LENGTH: 10 amino acids
           (B) TYPE: amino acid
           (C) STRANDEDNESS:
           (D) TOPOLOGY: unknown (ii) MOLECULE TYPE: peptide (xi) SEQUENCE DESCRIPTION: SEQ ID NO: 57:

Gln Gly Gly Asn Leu Val Arg His Leu Arg
                 5                  10

(2) INFORMATION FOR SEQ ID NO: 58:

(i) SEQUENCE CHARACTERISTICS:
           (A) LENGTH: 10 amino acids
           (B) TYPE: amino acid
           (C) STRANDEDNESS:
           (D) TOPOLOGY: unknown (ii) MOLECULE TYPE: peptide (xi) SEQUENCE DESCRIPTION: SEQ ID NO: 58:

Asn Gly Gly Asn Leu Gly Arg His Met Lys
                 5                  10

(2) INFORMATION FOR SEQ ID NO: 59:

(i) SEQUENCE CHARACTERISTICS:
           (A) LENGTH: 10 amino acids
           (B) TYPE: amino acid
           (C) STRANDEDNESS:
           (D) TOPOLOGY: unknown (ii) MOLECULE TYPE: peptide (xi) SEQUENCE DESCRIPTION: SEQ ID NO: 59:

Ala Arg Ser Asn Leu Leu Arg His Thr Arg
                 5                  10

(2) INFORMATION FOR SEQ ID NO: 60:

(i) SEQUENCE CHARACTERISTICS:
           (A) LENGTH: 10 amino acids
           (B) TYPE: amino acid
           (C) STRANDEDNESS:
           (D) TOPOLOGY: unknown (ii) MOLECULE TYPE: peptide (xi) SEQUENCE DESCRIPTION: SEQ ID NO: 60:

Leu Gln Ser Asn Leu Val Arg His Gln Arg
                 5                  10

(2) INFORMATION FOR SEQ ID NO: 61:

(i) SEQUENCE CHARACTERISTICS:
           (A) LENGTH: 10 amino acids
           (B) TYPE: amino acid
           (C) STRANDEDNESS:
           (D) TOPOLOGY: unknown (ii) MOLECULE TYPE: peptide (xi) SEQUENCE DESCRIPTION: SEQ ID NO: 61:

Ile Ala Ser Asn Leu Leu Arg His Gln Arg
                 5                  10

(2) INFORMATION FOR SEQ ID NO: 62:

(i) SEQUENCE CHARACTERISTICS:
```

(A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 62:

Asp Arg Ser Asn Leu Glu Arg His Thr Arg
                 5                  10

(2) INFORMATION FOR SEQ ID NO: 63:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 63:

Asn Gln Ser Asn Leu Glu Arg His His Arg
                 5                  10

(2) INFORMATION FOR SEQ ID NO: 64:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 64:

Gln Gln Ser Asn Leu Val Arg His Gln Arg
                 5                  10

(2) INFORMATION FOR SEQ ID NO: 65:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 65:

Asn Gly Gly Asn Leu Gly Arg His Met Lys
                 5                  10

(2) INFORMATION FOR SEQ ID NO: 66:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 66:

Asn Gly Ala Asn Leu Glu Arg His Arg Arg
                 5                  10

(2) INFORMATION FOR SEQ ID NO: 67:

(i) SEQUENCE CHARACTERISTICS:

(A) LENGTH: 10 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO: 67:

Ser Gln Gly Asn Leu Gln Arg His Gly Arg
                  5                  10

(2) INFORMATION FOR SEQ ID NO: 68:

(i) SEQUENCE CHARACTERISTICS:
            (A) LENGTH: 10 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO: 68:

Ser His Pro Asn Leu Asn Arg His Leu Lys
                  5                  10

(2) INFORMATION FOR SEQ ID NO: 69:

(i) SEQUENCE CHARACTERISTICS:
            (A) LENGTH: 10 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO: 69:

Thr Pro Gly Asn Leu Thr Arg His Gly Arg
                  5                  10

(2) INFORMATION FOR SEQ ID NO: 70:

(i) SEQUENCE CHARACTERISTICS:
            (A) LENGTH: 10 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO: 70:

Asp Arg Ser Asn Leu Glu Arg His Thr Arg
                  5                  10

(2) INFORMATION FOR SEQ ID NO: 71:

(i) SEQUENCE CHARACTERISTICS:
            (A) LENGTH: 10 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO: 71:

Asp His Ala Asn Leu Ala Arg His Thr Arg
                  5                  10

(2) INFORMATION FOR SEQ ID NO: 72:

(i) SEQUENCE CHARACTERISTICS:

(A) LENGTH: 10 amino acids
          (B) TYPE: amino acid
          (C) STRANDEDNESS:
          (D) TOPOLOGY: unknown (ii) MOLECULE TYPE: peptide (xi) SEQUENCE DESCRIPTION: SEQ ID NO: 72:

Asp Arg Ser Ser Leu Thr Arg His Thr Arg
                 5                  10

(2) INFORMATION FOR SEQ ID NO: 73:

(i) SEQUENCE CHARACTERISTICS:
          (A) LENGTH: 10 amino acids
          (B) TYPE: amino acid
          (C) STRANDEDNESS:
          (D) TOPOLOGY: unknown (ii) MOLECULE TYPE: peptide (xi) SEQUENCE DESCRIPTION: SEQ ID NO: 73:

Glu Arg Gly Thr Leu Ala Arg His Glu Lys
                 5                  10

(2) INFORMATION FOR SEQ ID NO: 74:

(i) SEQUENCE CHARACTERISTICS:
          (A) LENGTH: 10 amino acids
          (B) TYPE: amino acid
          (C) STRANDEDNESS:
          (D) TOPOLOGY: unknown (ii) MOLECULE TYPE: peptide (xi) SEQUENCE DESCRIPTION: SEQ ID NO: 74:

Asp Arg Arg Leu Leu Asp Arg His Gln Arg
                 5                  10

(2) INFORMATION FOR SEQ ID NO: 75:

(i) SEQUENCE CHARACTERISTICS:
          (A) LENGTH: 10 amino acids
          (B) TYPE: amino acid
          (C) STRANDEDNESS:
          (D) TOPOLOGY: unknown (ii) MOLECULE TYPE: peptide (xi) SEQUENCE DESCRIPTION: SEQ ID NO: 75:

Asp Arg Ser Ser Leu Thr Arg His Thr Arg
                 5                  10

(2) INFORMATION FOR SEQ ID NO: 76:

(i) SEQUENCE CHARACTERISTICS:
          (A) LENGTH: 10 amino acids
          (B) TYPE: amino acid
          (C) STRANDEDNESS:
          (D) TOPOLOGY: unknown (ii) MOLECULE TYPE: peptide (xi) SEQUENCE DESCRIPTION: SEQ ID NO: 76:

Glu Arg Thr Ser Leu Ser Arg His Ile Arg
                 5                  10

(2) INFORMATION FOR SEQ ID NO: 77:

(i) SEQUENCE CHARACTERISTICS:

(A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 77:

Ser Ala Gly Thr Leu Val Arg His Ser Lys
                 5                  10

(2) INFORMATION FOR SEQ ID NO: 78:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 78:

Gln Ala Gln Thr Leu Gln Arg His Leu Lys
                 5                  10

(2) INFORMATION FOR SEQ ID NO: 79:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 79:

Glu Lys Ala Thr Leu Ala Arg His Met Lys
                 5                  10

(2) INFORMATION FOR SEQ ID NO: 80:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 80:

Thr Gly Gly Ser Leu Ala Arg His Glu Arg
                 5                  10

(2) INFORMATION FOR SEQ ID NO: 81:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 81:

Arg Gln Ser Thr Leu Gly Arg His Thr Arg
                 5                  10

(2) INFORMATION FOR SEQ ID NO: 82:

(i) SEQUENCE CHARACTERISTICS:

(A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 82:

Glu Lys Ala Thr Leu Ala Arg His Met Lys
                 5                   10

(2) INFORMATION FOR SEQ ID NO: 83:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 83:

Gln Ala Gln Thr Leu Gln Arg His Leu Lys
                 5                   10

(2) INFORMATION FOR SEQ ID NO: 84:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 84:

Glu Arg Gly Thr Leu Ala Arg His Glu Lys
                 5                   10

(2) INFORMATION FOR SEQ ID NO: 85:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 85:

Gly Arg Asp Ala Leu Ala Arg His Gln Lys
                 5                   10

(2) INFORMATION FOR SEQ ID NO: 86:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 86:

Arg Gly Pro Asp Leu Ala Arg His Gly Arg
                 5                   10

(2) INFORMATION FOR SEQ ID NO: 87:

(i) SEQUENCE CHARACTERISTICS:

(A) LENGTH: 10 amino acids
          (B) TYPE: amino acid
          (C) STRANDEDNESS:
          (D) TOPOLOGY: unknown (ii) MOLECULE TYPE: peptide (xi) SEQUENCE DESCRIPTION: SEQ ID NO: 87:

Ser Arg Asp Val Leu Arg Arg His Asn Arg
                 5                  10

(2) INFORMATION FOR SEQ ID NO: 88:

(i) SEQUENCE CHARACTERISTICS:
          (A) LENGTH: 10 amino acids
          (B) TYPE: amino acid
          (C) STRANDEDNESS:
          (D) TOPOLOGY: unknown (ii) MOLECULE TYPE: peptide (xi) SEQUENCE DESCRIPTION: SEQ ID NO: 88:

Arg Arg Asp Val Leu Met Asn His Ile Arg
                 5                  10

(2) INFORMATION FOR SEQ ID NO: 89:

(i) SEQUENCE CHARACTERISTICS:
          (A) LENGTH: 10 amino acids
          (B) TYPE: amino acid
          (C) STRANDEDNESS:
          (D) TOPOLOGY: unknown (ii) MOLECULE TYPE: peptide (xi) SEQUENCE DESCRIPTION: SEQ ID NO: 89:

Arg Lys Asp Val Leu Val Ser His Val Arg
                 5                  10

(2) INFORMATION FOR SEQ ID NO: 90:

(i) SEQUENCE CHARACTERISTICS:
          (A) LENGTH: 10 amino acids
          (B) TYPE: amino acid
          (C) STRANDEDNESS:
          (D) TOPOLOGY: unknown (ii) MOLECULE TYPE: peptide (xi) SEQUENCE DESCRIPTION: SEQ ID NO: 90:

Arg Arg Asp Val Leu Met Asn His Ile Arg
                 5                  10

(2) INFORMATION FOR SEQ ID NO: 91:

(i) SEQUENCE CHARACTERISTICS:
          (A) LENGTH: 10 amino acids
          (B) TYPE: amino acid
          (C) STRANDEDNESS:
          (D) TOPOLOGY: unknown (ii) MOLECULE TYPE: peptide (xi) SEQUENCE DESCRIPTION: SEQ ID NO: 91:

Arg Glu Asp Ala Leu Thr Ser His Glu Arg
                 5                  10

(2) INFORMATION FOR SEQ ID NO: 92:

(i) SEQUENCE CHARACTERISTICS:

(A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 92:

Arg Val Asp Ala Leu Glu Ala His Arg Arg
                 5                  10

(2) INFORMATION FOR SEQ ID NO: 93:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 93:

Asp Arg Ser Ser Leu Thr Arg His Thr Arg
                 5                  10

(2) INFORMATION FOR SEQ ID NO: 94:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 94:

Glu Arg Thr Ser Leu Ser Arg His Ile Arg
                 5                  10

(2) INFORMATION FOR SEQ ID NO: 95:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 95:

Gly Ala Arg Ser Leu Thr Arg His Gln Arg
                 5                  10

(2) INFORMATION FOR SEQ ID NO: 96:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 96:

Thr Gly Gly Ser Leu Ala Arg His Glu Arg
                 5                  10

(2) INFORMATION FOR SEQ ID NO: 97:

(i) SEQUENCE CHARACTERISTICS:

(A) LENGTH: 10 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO: 97:

Gln Arg Ala Ser Leu Ala Ser His Met Arg
                5                   10

(2) INFORMATION FOR SEQ ID NO: 98:

(i) SEQUENCE CHARACTERISTICS:
            (A) LENGTH: 10 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO: 98:

Asn Arg Asp Thr Leu Thr Arg His Ser Lys
                5                   10

(2) INFORMATION FOR SEQ ID NO: 99:

(i) SEQUENCE CHARACTERISTICS:
            (A) LENGTH: 10 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO: 99:

Glu Arg Gly Thr Leu Ala Arg His Glu Arg
                5                   10

(2) INFORMATION FOR SEQ ID NO: 100:

(i) SEQUENCE CHARACTERISTICS:
            (A) LENGTH: 10 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO: 100:

Arg Gly Asp Ala Leu Thr Ser His Glu Arg
                5                   10

(2) INFORMATION FOR SEQ ID NO: 101:

(i) SEQUENCE CHARACTERISTICS:
            (A) LENGTH: 10 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO: 101:

Arg Ala Asp Ala Leu Met Val His Lys Arg
                5                   10

(2) INFORMATION FOR SEQ ID NO: 102:

(i) SEQUENCE CHARACTERISTICS:

(A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 102:

Arg Gln Asp Thr Leu Val Gly His Glu Arg
                 5                  10

(2) INFORMATION FOR SEQ ID NO: 103:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 103:

Arg Gln Ser Thr Leu Val Arg His Thr Arg
                 5                  10

(2) INFORMATION FOR SEQ ID NO: 104:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 104:

Arg Ala Ala Asp Leu Asn Arg His Val Arg
                 5                  10

(2) INFORMATION FOR SEQ ID NO: 105:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 105:

Arg Lys Asp Val Leu Val Ser His Val Arg
                 5                  10

(2) INFORMATION FOR SEQ ID NO: 106:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 106:

Arg Arg Asp Val Leu Met Asn His Ile Arg
                 5                  10

(2) INFORMATION FOR SEQ ID NO: 107:

(i) SEQUENCE CHARACTERISTICS:

(A) LENGTH: 10 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO: 107:

Arg Ser Asp Thr Leu Lys Lys His Gly Lys
                 5                  10

(2) INFORMATION FOR SEQ ID NO: 108:

(i) SEQUENCE CHARACTERISTICS:
            (A) LENGTH: 10 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO: 108:

Arg Gly Pro Asp Leu Ala Arg His Gly Arg
                 5                  10

(2) INFORMATION FOR SEQ ID NO: 109:

(i) SEQUENCE CHARACTERISTICS:
            (A) LENGTH: 10 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO: 109:

Ala Arg Glu Val Leu Gln Arg His Thr Arg
                 5                  10

(2) INFORMATION FOR SEQ ID NO: 110:

(i) SEQUENCE CHARACTERISTICS:
            (A) LENGTH: 10 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO: 110:

Arg Glu Asp Val Leu Ile Arg His Gly Lys
                 5                  10

(2) INFORMATION FOR SEQ ID NO: 111:

(i) SEQUENCE CHARACTERISTICS:
            (A) LENGTH: 10 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO: 111:

Arg Ser Asp Leu Leu Gln Arg His His Lys
                 5                  10

(2) INFORMATION FOR SEQ ID NO: 112:

(i) SEQUENCE CHARACTERISTICS:

```
          (A) LENGTH: 10 amino acids
          (B) TYPE: amino acid
          (C) STRANDEDNESS:
          (D) TOPOLOGY: unknown (ii) MOLECULE TYPE: peptide (xi) SEQUENCE DESCRIPTION: SEQ ID NO: 112:

Arg Leu Asp Gly Leu Arg Thr His Leu Lys
                 5                  10

(2) INFORMATION FOR SEQ ID NO: 113:

(i) SEQUENCE CHARACTERISTICS:
          (A) LENGTH: 10 amino acids
          (B) TYPE: amino acid
          (C) STRANDEDNESS:
          (D) TOPOLOGY: unknown (ii) MOLECULE TYPE: peptide (xi) SEQUENCE DESCRIPTION: SEQ ID NO: 113:

Arg Gly Asp Ala Leu Thr Ser His Glu Arg
                 5                  10

(2) INFORMATION FOR SEQ ID NO: 114:

(i) SEQUENCE CHARACTERISTICS:
          (A) LENGTH: 10 amino acids
          (B) TYPE: amino acid
          (C) STRANDEDNESS:
          (D) TOPOLOGY: unknown (ii) MOLECULE TYPE: peptide (xi) SEQUENCE DESCRIPTION: SEQ ID NO: 114:

Arg Ala Asp Ala Leu Met Val His Lys Arg
                 5                  10

(2) INFORMATION FOR SEQ ID NO: 115:

(i) SEQUENCE CHARACTERISTICS:
          (A) LENGTH: 10 amino acids
          (B) TYPE: amino acid
          (C) STRANDEDNESS:
          (D) TOPOLOGY: unknown (ii) MOLECULE TYPE: peptide (xi) SEQUENCE DESCRIPTION: SEQ ID NO: 115:

Arg Val Asp Ala Leu Glu Ala His Arg Arg
                 5                  10

(2) INFORMATION FOR SEQ ID NO: 116:

(i) SEQUENCE CHARACTERISTICS:
          (A) LENGTH: 10 amino acids
          (B) TYPE: amino acid
          (C) STRANDEDNESS:
          (D) TOPOLOGY: unknown (ii) MOLECULE TYPE: peptide (xi) SEQUENCE DESCRIPTION: SEQ ID NO: 116:

Arg Arg Asp Val Leu Leu Asn His Ile Arg
                 5                  10

(2) INFORMATION FOR SEQ ID NO: 117:

(i) SEQUENCE CHARACTERISTICS:
```

(A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 117:

Arg Glu Asp Val Leu Ile Arg His Gly Lys
                 5                  10

(2) INFORMATION FOR SEQ ID NO: 118:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 118:

Arg Ser Asp Leu Leu Gln Arg His His Lys
                 5                  10

(2) INFORMATION FOR SEQ ID NO: 119:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 119:

Lys Ala Ser Asn Leu Val Ser His Ile Arg
                 5                  10

(2) INFORMATION FOR SEQ ID NO: 120:

(i) SEQUENCE CHARACTERISTICS:
        (A) LENGTH: 10 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO: 120:

Leu Arg His Asn Leu Glu Thr His Met Arg
                 5                  10

(2) INFORMATION FOR SEQ ID NO: 121:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 121:

CGCAGAAGCC                                                          10

(2) INFORMATION FOR SEQ ID NO: 122:

(i) SEQUENCE CHARACTERISTICS:
        (A) LENGTH: 10 base pairs
        (B) TYPE: nucleic acid
        (C) STRANDEDNESS: single

```
            (D) TOPOLOGY: linear (xi) SEQUENCE DESCRIPTION: SEQ ID NO: 122:

TCCAGAAGCC                                                                    10

(2) INFORMATION FOR SEQ ID NO: 123:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO: 123:

CGCAGGTGAG                                                                    10

(2) INFORMATION FOR SEQ ID NO: 124:

(i) SEQUENCE CHARACTERISTICS:
            (A) LENGTH: 11 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO: 124:

Glu Gln Lys Leu Ile Ser Glu Glu Asp Leu Asn
                  5                      10

(2) INFORMATION FOR SEQ ID NO: 125:

(i) SEQUENCE CHARACTERISTICS:
            (A) LENGTH: 7 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO: 125:

Pro Lys Lys Lys Arg Lys Val
```

BINDING PROTEINS FOR RECOGNITION OF DNA

This is a continuation of application No. 08/793,408, filed Jun. 2, 1997, which is a 371 of PCT/GB95/01949, filed Aug. 17, 1995.

FIELD OF THE INVENTION

This invention relates inter alia to methods of selecting and designing polypeptides comprising zinc finger binding motifs, polypeptides made by the method(s) of the invention and to various applications thereof.

BACKGROUND OF THE INVENTION

Selective gene expression is mediated via the interaction of protein transcription factors with specific nucleotide sequences within the regulatory region of the gene. The most widely used domain within protein transcription factors appears to be the zinc finger (Zf) motif. This is an independently folded zinc-containing mini-domain which is used in a modular repeating fashion to achieve sequence-specific recognition of DNA (Klug 1993 Gene 135, 83–92). The first zinc finger motif was identified in the Xenopus transcription factor TFIIIA (Miller et al., 1985 EMBO J. 4, 1609–1614). The structure of Zf proteins has been determined by NMR studies (Lee et al., 1989 Science 245, 635–637) and crystallography (Pavletich & Pabo, 1991 Science 252, 809–812).

The manner in which DNA-binding protein domains are able to discriminate between different DNA sequences is an important question in understanding crucial processes such as the control of gene expression in differentiation and development. The zinc finger motif has been studied extensively, with a view to providing, some insight into this problem, owing to its remarkable prevalence in the eukaryotic genome, and its important role in proteins which control gene expression in Drosophila (e.g,. Harrison & Travers 1990 EMBO J. 9, 207–216), the mouse (Christy et al., 1988 Proc. Natl. Acad. Sci. USA 85, 7857–786 1) and humans (Kinzler et al., 1988 Nature (London) 332, 371).

Most sequence-specific DNA-binding proteins bind to the DNA double helix by inserting an α-helix into the major groove (Pabo & Sauer 1992 Annu. Rev. Biochem. 61. 1053–1095; Harrison 1991 Nature (London) 353, 715–719; and Klug 1993 Gene 135, 83–92). Sequence specificity results from the geometrical and chemical complementarity between the amino acid side chains of the α-helix and the accessible groups exposed on the edges of base-pairs. In addition to this direct reading of the DNA sequence, interactions with the DNA backbone stabilise the complex and are sensitive to the conformation of the nucleic acid, which in turn depends on the base sequence (Dickerson & Drew 1981 J. Mol. Biol. 149, 761–786). A priori, a simple set of rules might suffice to explain the specific association of protein and DNA in all complexes, based on the possibility that certain amino acid side chains have preferences for particular base-pairs. However, crystal structures of protein-DNA complexes have shown that proteins can be idiosyncratic in their mode of DNA recognition, at least partly because they may use alternative geometries to present their sensory α-helices to DNA, allowing a variety of different base contacts to be made by a single amino acid and vice versa (Matthews 1988 Nature (London) 335, 294–295).

Mutagenesis of Zf proteins has confirmed modularity of the domains. Site directed mutagenesis has been used to change key Zf residues, identified through sequence homology alignment, and from the structural data, resulting in altered specificity of Zf domain (Nardelli et al., 1992 NAR 26, 4137–4144). The authors suggested that although design of novel binding specificities would be desirable, design would need to take into account sequence and structural data. They state "there is no prospect of achieving a zinc finger recognition code".

Despite this, many groups have been trying to work towards such a code, although only limited rules have so far been proposed. For example, Desjarlais et al., (1992b PNAS 89, 7345–7349) used systematic mutation of two of the three contact residues (based on consensus sequences) in finger two of the polypeptide Sp1 to suggest that a limited degenerate code might exist. Subsequently the authors used this to design three Zf proteins with different binding specificities and affinities (Desjarlais & Berg, 1993 PNAS 90, 2250–2260). They state that the design of Zf proteins with predictable specificities and affinities "may not always be straightforward".

We believe the zinc finger of the TFIIIA class to be a good candidate for deriving a set of more generally applicable specificity rules owing to its great simplicity of structure and interaction with DNA. The zinc finger is an independently folding domain which uses a zinc ion to stabilise the packing of an antiparallel β-sheet against an α-helix (Miller et al., 1985 EMBO J. 4, 1609–1614; Berg 1988 Proc. Natl. Acad. Sci. USA 85, 99–102; and Lee et al., 1989 Science 245, 635–637). The crystal structures of zinc finger-DNA complexes show a semiconserved pattern of interactions in which 3 amino acids from the α-helix contact 3 adjacent bases (a triplet) in DNA (Pavletich & Pabo 1991 Science 252, 809–817; Fairall et al., 1993 Nature (London) 366, 483–487; and Pavletich & Pabo 1993 Science 261, 1701–1707). Thus the mode of DNA recognition is principally a one-to-one interaction between amino acids and bases. Because zinc fingers function as independent modules (Mlller et al., 1985 EMBO J. 4, 1609–1614; Kiug & Rhodes 1987 Trends Biochem. Sci. 12, 464–469), it should be possible for fingers with different triplet specificities to be combined to give specific recognition of longer DNA sequences. Each finger is folded so that three amino acids are presented for binding to the DNA target sequence, although binding may be directly through only two of these positions. In the case of Zif268 for example, the protein is made up of three fingers which contact a 9 base pair contiguous sequence of target DNA. A linker sequence is found between fingers which appears to make no direct contact with the nucleic acid.

Protein engineering experiments have shown that it is possible to alter rationally the DNA-binding characteristics of individual zinc fingers when one or more of the α-helical positions is varied in a number of proteins (Nardelli et al., 1991 Nature (London) 349, 175–178; Nardelli et al., 1992 Nucleic Acids Res. 20, 4137–4144; and Desjarlais & Berg 1992a Proteins 13, 272). It has already been possible to propose some principles relating amino acids on the α-helix to corresponding bases in the bound DNA sequence (Desjarlais & Berg 1992b Proc. Natl. Acad. Sci. USA 89, 7345–7349). However in this approach the altered positions on the a-helix are prejudged, making it possible to overlook the role of positions which are not currently considered important; and secondly, owing to the importance of context, concomitant alterations are sometimes required to affect specificity (Desjarlais & Berg 1992b), so that a significant correlation between an amino acid and base may be misconstrued.

To investigate binding of mutant Zf proteins, Thiesen and Bach (1991 FEBS 283, 23–26) mutated Zf fingers and studied their binding to randomised oligonucleotides, using electrophoretic mobility shift assays. Subsequent use of phage display technology has permitted the expression of random libraries of Zf mutant proteins on the surface of bacteriophage. The three Zf domains of Zif268, with 4 positions within finger one randomised, have been displayed on the surface of filamentous phage by Rebar and Pabo (1994 Science 263, 671–673). The library was then subjected to rounds of affinity selection by binding to target DNA oligonucleotide sequences in order to obtain Zf proteins with new binding specificities. Randomised mutagenesis (at the same postions as those selected by Rebar & Pabo) of finger 1 of Zif 268 with phage display has also been used by Jamieson et al., (1994 Biochemistry 33, 5689–5695) to create novel binding specificity and affinity.

More recently Wu et al. (1995 Proc. Natl. Acad. Sci. USA 92, 344–348) have made three libraries, each of a different finger from Zif268, and each having six or seven α-helical positions randomised. Six triplets were used in selections but did not return fingers with any sequence biases; and when the three triplets of the Zif268 binding site were individually used as controls, the vast majority of selected fingers did not resemble the sequences of the wild-type Zif268 fingers and, though capable of tight binding to their target sites in vitro, were usually not able to discriminate strongly against different triplets. The authors interpret the results as evidence against the existence of a code.

In summary, it is known that Zf protein motifs are widespread in DNA binding proteins and that binding is via three key amino acids, each one contacting a single base pair in the target DNA sequence. Motifs are modular and may be linked together to form a set of fingers which recognise a contiguous DNA sequence (e.g. a three fingered protein will recognise a 9mer etc). The key residues involved in DNA binding have been identified through sequence data and from structural information. Directed and random mutagenesis has confirmed the role of these amino acids in determining specificity and affinity. Phage display has been used to screen for new binding specificities of random mutants of fingers. A recognition code, to aid design of new finger specificities, has been worked towards although it has been suggested that specificity may be difficult to predict.

SUMMARY OF THE INVENTION

In a first aspect the invention provides a library of DNA sequences, each sequence encoding at least one zinc finger binding motif for display on a viral particle, the sequences coding for zinc finger binding motifs having random allocation of amino acids at positions −1, +2, +3, +6 and at least at one of positions +1, +5 and +8.

A zinc finger binding motif is the α-helical structural motif found in zinc finger binding proteins, well known to those skilled in the art. The above numbering is based on the first amino acid in the α-helix of the zinc finger binding motif being position +1. It will be apparent to those skilled in the art that the amino acid residue at position −1 does not, strictly speaking, form part of the α-helix of the zinc binding finger motif. Nevertheless, the residue at −1 is shown to be very important functionally and is therefore considered as part of the binding motif α-helix for the purposes of the present invention.

The sequences may code for zinc finger binding motifs having random allocation at all of positions +1, +5 and +8. The sequences may also be randomised at other positions (e.g. at position +9, although it is generally preferred to retain an arginine or a lysine residue at this position).

Further, whilst allocation of amino acids at the designated "random" positions may be genuinely random, it is preferred to avoid a hydrophobic residue (Phe, Trp or Tyr) or a cysteine residue at such positions.

Preferably the zinc finger binding motif is present within the context of other amino acids (which may be present in zinc finger proteins), so as to form a zinc finger (which includes an antiparallel β-sheet). Further, the zinc finger is preferably displayed as part of a zinc finger polypeptide, which polypeptide comprises a plurality of zinc fingers joined by an intervening linker peptide. Typically the library of sequences is such that the zinc finger polypeptide will comprise two or more zinc fingers of defined amino acid sequence (generally the wild type sequence) and one zinc finger having a zinc finger binding motif randomised in the manner defined above. It is preferred that the randomised finger of the polypeptide is positioned between the two or more fingers having defined sequence. The defined fingers will establish the "phase" of binding of the polypeptide to DNA, which helps to increase the binding specificity of the randomised finger.

Preferably the sequences encode the randomised binding motif of the middle finger of the Zif268 polypeptide. Conveniently, the sequences also encode those amino acids N-terminal and C-terminal of the middle finger in wild type Zif268, which encode the first and third zinc fingers respectively. In a particular embodiment, the sequence encodes the whole of the Zif268 polypeptide. Those skilled in the art will appreciate that alterations may also be made to the sequence of the linker peptide and/or the β-sheet of the zinc finger polypeptide.

In a further aspect, the invention provides a library of DNA sequences, each sequence encoding the zinc finger binding motif of at least a middle finger of a zinc finger binding polypeptide for display on a viral particle, the sequences coding for the binding motif having random allocation of amino acids at positions −1, +2, +3 and +6. Conveniently, the zinc finger polypeptide will be Zif268.

Typically, the sequences of either library are such that the zinc finger binding domain can be cloned as a fusion with the minor coat protein (pIII) of bacteriophage fd. Conveniently, the encoded polypeptide includes the tripeptide sequence Met-Ala-Glu as the N terminal of the zinc finger domain, which is known to allow expression and display using the bacteriophage fd system. Desirably the library comprises $10^6$ or more different sequences (ideally, as many as is practicable).

In another aspect the invention provides a method of designing a zinc finger polypeptide for binding to a particular target DNA sequence, comprising screening each of a plurality of zinc finger binding motifs against at least an effective portion of the target DNA sequence, and selecting those motifs which bind to the target DNA sequence. An effective portion of the target DNA sequence is a sufficient length of DNA to allow binding of the zinc binding motif to the DNA. This is the minimum sequence information (concerning the target DNA sequence) that is required. Desirably at least two, preferably three or more, rounds of screening are performed.

The invention also provides a method of designing a zinc finger polypeptide for binding to a particular target DNA sequence, comprising comparing the binding of each of a plurality of zinc finger binding motifs to one or more DNA triplets, and selecting those motifs exhibiting preferable binding characteristics. Preferably the method defined immediately above is preceded by a screening step according to the method defined in the previous paragraph.

It is thus preferred that there is a two-step selection procedure: the first step comprising screening each of a plurality of zinc finger binding motifs (typically in the form of a display library), mainly or wholly on the basis of affinity for the target sequence; the second step comprising comparing binding characteristics of those motifs selected by the initial screening step, and selecting those having preferable binding characteristics for a particular DNA triplet.

Where the plurality of zinc finger binding motifs is screened against a single DNA triplet, it is preferred that the triplet is represented in the target DNA sequence at the appropriate postion. However, it is also desirable to compare the binding of the plurality of zinc binding motifs to one or more DNA triplets not represented in the target DNA sequence (e.g. differing by just one of the three base pairs) in order to compare the specificity of binding of the various binding motifs. The plurality of zinc finger binding motifs may be screened against all 64 possible permutations of 3 DNA bases.

Once suitable zinc finger binding motifs have been identified and obtained, they will advantageously be combined in a single zinc finger polypeptide. Typically this will be accomplished by use of recombinant DNA technology; conveniently a phage display system may be used.

In another aspect, the invention provides a DNA library consisting of 64 sequences, each sequence comprising a different one of the 64 possible permutations of three DNA bases in a form suitable for use in the selection method defined above. Desirably the sequences are associated, or capable of being associated, with separation means. Advantageously, the separation means is selected from one of the following: microtitre plate; magnetic beads; or affinity chromatography column. Conveniently the sequences are biotinylated. Preferably the sequences are contained within 12 mini-libraries, as explained elsewhere.

In a further aspect the invention provides a zinc finger polypeptide designed by one or both of the methods defined above. Preferably the zinc finger polypeptide designed by the method comprises a combination of a plurality of zinc fingers (adjacent zinc fingers being joined by an intervening linker peptide), each finger comprising a zinc finger binding motif. Desirably, each zinc finger binding motif in the zinc finger polypeptide has been selected for preferable binding characteristics by the method defined above. The intervening linker peptide may be the same between each adjacent zinc finger or, alternatively, the same zinc finger polypeptide may contain a number of different linker peptides. The intervening linker peptide may be one that is present in naturally-occurring zinc finger polypeptides or may be an artificial sequence. In particular, the sequence of the intervening linker peptide may be varied, for example, to optimise binding of the zinc finger polypeptide to the target sequence.

Where the zinc finger polypeptide comprises a plurality of zinc binding motifs, it is preferred that each motif binds to those DNA triplets which represent contiguous or substantially contiguous DNA in the sequence of interest. Where several candidate binding motifs or candidate combinations of motifs exist, these may be screened against the actual target sequence to determine the optimum composition of the polypeptide. Competitor DNA may be included in the screening assay for comparison, as described below.

The non-specific component of all protein-DNA interactions, which includes contacts to the sugar-phosphate backbone as well as ambiguous contacts to base-pairs, is a considerable driving force towards complex formation and can result in the selection of DNA-binding proteins with reasonable affinity but without specificity for a given DNA sequence. Therefore, in order to minimise these non-specific interactions when designing a polypeptide, selections should preferably be performed with low concentrations of specific binding site in a background of competitor DNA, and binding should desirably take place in solution to avoid local concentration effects and the avidity of multivalent phage for ligands immobilised on solid surfaces.

As a safeguard against spurious selections, the specificity of individual phage should be determined following the final round of selection. Instead of testing for binding to a small number of binding sites, it would be desirable to screen all possible DNA sequences.

It has now been shown possible by the present inventors (below) to design a truly modular zinc binding polypeptide, wherein the zinc binding motif of each zinc binding finger is selected on the basis of its affinity for a particular triplet. Accordingly, it should be well within the capability of one of normal skill in the art to design a zinc finger polypeptide capable of binding to any desired target DNA sequence simply by considering the sequence of triplets present in the target DNA and combining in the appropriate order zinc fingers comprising zinc finger binding motifs having the necessary binding characteristics to bind thereto. The greater the length of known sequence of the target DNA, the greater the number of zinc finger binding motifs that can be included in the zinc finger polypeptide. For example, if the known sequence is only 9 bases long then three zinc finger binding motifs can be included in the polypeptide. If the known sequence is 27 bases long then, in theory, up to nine binding motifs could be included in the polypeptide. The longer the target DNA sequence, the lower the probability of its occurrence in any given portion of DNA.

Moreover, those motifs selected for inclusion in the polypeptide could be artificially modified (e.g. by directed mutagenesis) in order to optimise further their binding characteristics. Alternatively (or additionally) the length and amino acid sequence of the linker peptide joining adjacent zinc binding fingers could be varied, as outlined above. This may have the effect of altering the position of the zinc finger binding motif relative to the DNA sequence of interest, and thereby exert a further influence on binding characteristics.

Generally, it will be preferred to select those motifs having high affinity and high specificity for the target triplet.

In a further aspect, the invention provides a kit for making a zinc finger polypeptide for binding to a nucleic acid sequence of interest, comprising: a library of DNA sequences encoding zinc finger binding motifs of known binding characteristics in a form suitable for cloning into a vector; a vector molecule suitable for accepting one or more sequences from the library; and instructions for use.

Preferably the vector is capable of directing the expression of the cloned sequences as a single zinc finger polypeptide. In particular it is preferred that the vector is capable of directing the expression of the cloned sequences as a single zinc finger polypeptide displayed on the surface of a viral particle, typically of the sort of viral display particle which are known to those skilled in the art. The DNA sequences are preferably in such a form that the expressed polypeptides are capable of self-assembling into a number of zinc finger polypeptides.

It wil be apparent that the kit defined above will be of particular use in designing a zinc finger polypeptide comprising a plurality of zinc finger binding motifs, the binding characteristics of which are already known. In another aspect the invention provides a kit for use when zinc finger binding motifs with suitable binding characteristics have not yet been identified, such that the invention provides a kit for making a zinc finger polypeptide for binding to a nucleic acid sequence of interest, comprising: a library of DNA sequences, each encoding a zinc finger binding motif in a form suitable for screening and/or selecting according to the methods defined above; and instructions for use.

Advantageously, the library of DNA sequences in the kit will be a library in accordance with the first aspect of the invention. Conveniently, the kit may also comprise a library of 64 DNA sequences, each sequence comprising a different one of the 64 possible permutations of three DNA bases, in a form suitable for use in the selection method defined previously. Typically, the 64 sequences are present in 12 separate mini-libraries, each mini-library having one postion in the relevant triplet fixed and two postions randomised. Preferably, the kit will also comprise appropriate buffer solutions, and/or reagents for use in the detection of bound zinc fingers. The kit may also usefully include a vector suitable for accepting one or more sequences selected from the library of DNA sequences encoding zinc finger binding motifs.

In a preferred embodiment, the present teaching will be used for isolating the genes for the middle zinc fingers which, having been previously selected by one of the 64 triplets, are thought to have specific DNA binding activity. The mixture of genes specifying fingers which bind to a given triplet will be amplified by PCR using three sets of primers. The sets will have unique restriction sites, which will define the assembly of zinc fingers into three finger polypeptides. The appropriate reagents are preferably provided in kit form.

For instance, the first set of primers might have SfiI and AgeI sites, the second set AgeI and EagI sites and third set EagI and NotI sites. It will be noted that the "first" site will preferably be SfiI, and the "last" site NotI, so as to facilitate cloning into the SfiI and NotI sites of the phage vector. To assemble a library of three finger proteins which recognise the sequence AAAGGGGGG, the fingers selected by the triplet GGG are amplified using the first two sets of primers and ligated to the fingers selected by the triplet AAA amplified using the third set of primers. The combinatorial library is cloned on the surface of phage and a nine base-pair site can be used to select the best combination of fingers en bloc.

The genes for fingers which bind to each of the 64 triplets can be amplified by each set of primers and cut using the appropriate restriction enzymes. These building blocks for three-finger proteins can be sold as components of a kit for use as described above. The same could be done for the library amplified with different primers so that 4- or 5- finger proteins could be built.

Additionally a large (pre-assembled) library of all combinations of the fingers selected by all triplets can also be developed for single-step selection of DNA-binding proteins using 9 bp, or much longer, DNA fragments. For this particular application, which will require very large libraries of novel 3-finger proteins, it may be preferable to use methods of selection other than phage display; for example stalled polysomes (developed by Affimax) where protein and mRNA become linked.

In a further aspect the invention provides a method of altering the expression of a gene of interest in a target cell, comprising: determining (if necessary) at least part of the DNA sequence of the structural region and/or a regulatory region of the gene of interest; designing a zinc finger polypeptide to bind to the DNA of known sequence, and causing said zinc finger polypeptide to be present in the target cell, (preferably in the nucleus thereof). (It will be apparent that the DNA sequence need not be determined if it is already known.)

The regulatory region could be quite remote from the structural region of the gene of interest (e.g. a distant enhancer sequence or similar). Preferably the zinc finger polypeptide is designed by one or both of the methods of the invention defined above.

Binding of the zinc finger polypeptide to the target sequence may result in increased or reduced expression of the gene of interest depending, for example, on the nature of the target sequence (e.g. structural or regulatory) to which the polypeptide binds.

In addition, the zinc finger polypeptide may advantageously comprise functional domains from other proteins (e.g. catalytic domains from restriction enzymes, recombinases, replicases, integrases and the like) or even "synthetic" effector domains. The polypeptide may also comprise activation or processing signals, such as nuclear localisation signals. These are of particular usefulness in targtetting the polypeptide to the nucleus of the cell in order to enhance the binding of the polypeptide to an intranuclear target (such as genomic DNA). A particular example of such a localisation signal is that from the large T antigen of SV40. Such other functional domains/signals and the like are conveniently present as a fusion with the zinc finger polypeptide. Other desirable fusion partners comprise immunoglobulins or fragments thereof (eg. Fab, scFv) having binding activity.

The zinc finger polypeptide may be synthesised in situ in the cell as a result of delivery to the cell of DNA directing expression of the polypeptide. Methods of facilitating delivery of DNA are well-known to those skilled in the art and include, for example, recombinant viral vectors (e.g. retroviruses, adenoviruses), liposomes and the like. Alternatively, the zinc finger polypeptide could be made outside the cell and then delivered thereto. Delivery could be facilitated by incorporating the polypeptide into liposomes etc. or by attaching the polypeptide to a targetting moiety (such as the binding portion of an antibody or hormone molecule). Indeed, one significant advantage of zinc finger proteins over oligonucleotides or protein-nucleic acids (PNAs) in controlling gene expression, would be the vector-free delivery of protein to target cells. Unlike the above, many examples of soluble proteins entering cells are known, including antibodies to cell surface receptors. The present inventors are currently carrying out fusions of anti-bcr-abl fingers (see example 3 below) to a single-chain (sc) Fv fragment capable of recognising NIP (4-hydroxy-5-iodo-3-nitrophenyl acetyl). Mouse transferrin conjugated with NIP will be used to deliver the fingers to mouse cells via the mouse transferrin receptor.

Media (e.g. microtitre wells, resins etc.) coated with NIP can also be used as solid supports for zinc fingers fused to anti-NIP scFvs, for applications requiring immobilised zinc fingers (e.g. the purification of specific nucleic acids).

In a particular embodiment, the invention provides a method of inhibiting cell division by causing the presence in a cell of a zinc finger polypeptide which inhibits the expression of a gene enabling the cell to divide.

In a specific embodiment, the invention provides a method of treating a cancer, comprising delivering to a patient, or causing to be present therein, a zinc finger polypeptide which inhibits the expression of a gene enabling the cancer cells to divide. The target could be, for example, an oncogene or a normal gene which is overexpressed in the cancer cells.

To the best knowledge of the inventors, design of a zinc finger polypeptide and its successful use in modulation of gene expression (as described below) has never previously been demonstrated. This breakthrough presents numerous possibilities. In particular, zinc finger polypeptides could be designed for therapeutic and/or prophylactic use in regulating the expression of disease-associated genes. For example, zinc finger polypeptides could be used to inhibit the expression of foreign genes (e.g. the genes of bacterial or viral pathogens) in man or animals, or to modify the expression of mutated host genes (such as oncogenes).

The invention therefore provides a zinc finger polypeptide capable of inhibiting the expression of a disease-associated gene. Typically the zinc finger polypeptide will not be a naturally-occurring polypeptide but will be specifically designed to inhibit the expression of the disease-associated gene. Conveniently the polypeptide will be designed by one or both of the methods of the invention defined above. Advantageously the disease-associated gene will be an oncogene, typically the BCR-ABL fusion oncogene or a ras oncogene. In a particular embodiment the invention provides a zinc finger polypeptide designed to bind to the DNA sequence GCAGAAGCC and capable of inihibting the expression of the BCR-ABL fusion oncogene.

In yet another aspect the invention provides a method of modifying a nucleic acid sequence of interest present in a sample mixture by binding thereto a zinc finger polypeptide, comprising contacting the sample mixture with a zinc finger polypeptide having affinity for at least a portion of the sequence of interest, so as to allow the zinc finger polypeptide to bind specifically to the sequence of interest.

The term "modifying" as used herein is intended to mean that the sequence is considered modified simply by the binding of the zinc finger polypeptide. It is not intended to suggest that the sequence of nucleotides is changed, although such changes (and others) could ensue following binding of the zinc finger polypeptide to the nucleic acid of interest. Conveniently the nucleic acid sequence is DNA.

Modification of the nucleic acid of interest (in the sense of binding thereto by a zinc finger polypeptide) could be detected in any of a number of methods (e.g. gel mobility shift assays, use of labelled zinc finger polypeptides—labels could include radioactive, fluorescent, enzyme or biotin/streptavidin labels).

Modification of the nucleic acid sequence of interest (and detection thereof) may be all that is required (e.g. in diagnosis of disease). Desirably however, further processing of the sample is performed. Conveniently the zinc finger polypeptide (and nucleic acid sequences specifically bound thereto) are separated from the rest of the sample. Advantageously the zinc finger polypeptide is bound to a solid phase support, to facilitate such separation. For example, the zinc finger polypeptide may be present in an acrylamide or agarose gel matrix or, more preferably, is immobilised on the surface of a membrane or in the wells of a microtitre place.

Possible uses of suitably designed zinc finger polypeptides are:

a) Therapy (e.g. targetting to double stranded DNA)
b) Diagnosis (e.g. detecting mutations in gene sequences: the present work has shown that "tailor made" zinc finger polypeptides can distinguish DNA sequences differing by one base pair).
c) DNA purification (the zinc finger polypeptide could be used to purify restriction fragments from solution, or to visualise DNA fragments on a gel [for example, where the polypeptide is linked to an appropriate fusion partner, or is detected by probing with an antibody]).

In addition, zinc finger polypeptides could even be targeted to other nucleic acids such as ss or ds RNA (e.g. self-complementary RNA such as is present in many RNA molecules) or to RNA-DNA hybrids, which would present another possible mechanism of affecting cellular events at the molecular level.

In Example 1 the inventors describe and successfully demonstrate the use of the phage display technique to construct and screen a random zinc finger binding motif library, using a defined oligonucleotide target sequence.

In Example 2 is disclosed the analysis of zinc finger binding motif sequences selected by the screening procedure of Example 1, the DNA-specificity of the motifs being studied by binding to a mini-library of randomised DNA target sequences to reveal a pattern of acceptable bases at each position in the target triplet—a "binding site signature".

In Example 3, the findings of the first two sections are used to select and modify rationally a zinc finger binding polypeptide in order to bind to a particular DNA target with high affinity: it is convincingly shown that the peptide binds to the target sequence and can modify gene expression in cells cultured in vitro.

Example 4 describes the development of an alternative zinc finger binding motif library.

Example 5 describes the design of a zinc finger binding polypeptide which binds to a DNA sequence of special clinical significance.

The invention will now be further described by way of example and with reference to the accompanying drawings, of which:

FIG. 2 shows three zinc fingers (Seq ID No. 2) used in the phage display library;

FIG. 4 is a "checker board" of binding site signatures determined for various zinc finger binding motifs (Seq ID No.s 19–51);

FIG. 6 shows the nucleotide sequence of the fusion between BCR and ABL sequences in p190 cDNA (Seq ID No. 9) and the corresponding exon boundaries in the BCR and ABL genes (Seq ID No.s 10–11);

FIG. 7 shows the amino acid sequences of various zinc finger binding motifs (Seq ID No.s 12–17) designed to test for binding to the BCR/ABL fusion;

FIGS. 10A–10C and 11 illustrate schematically different methods of designng zinc finger binding polypeptides.

EXAMPLE 1

Figure 1:
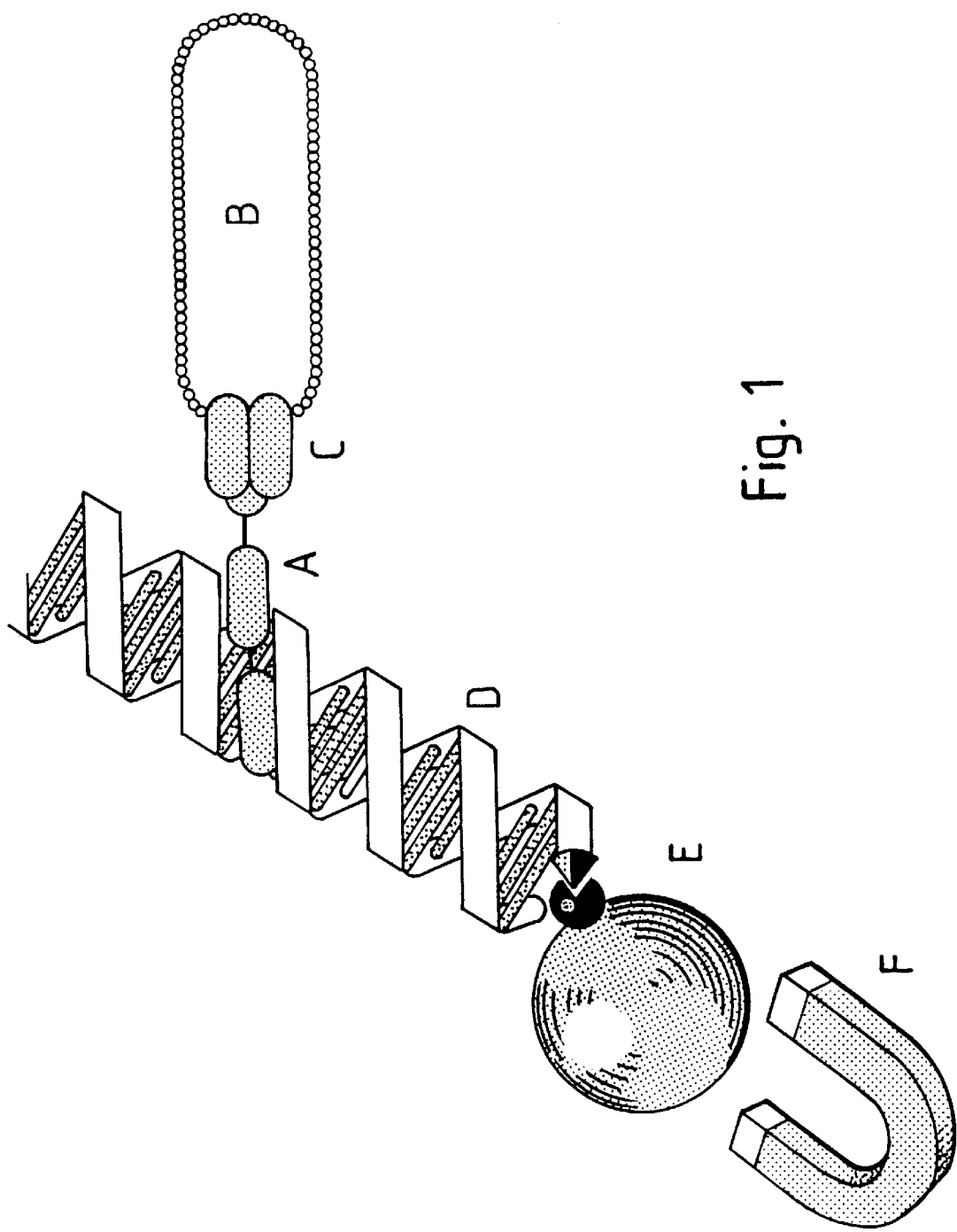
FIG. 1 is a schematic representation of affinity purification of phage particles displaying zinc finger binding motifs fused to phage coat proteins.

In this example the inventors have used a screening technique to study sequence-specific DNA recognition by zinc finger binding motifs. The example describes how a library of zinc finger binding motifs displayed on the surface of bacteriophage enables selection of fingers capable of binding to given DNA triplets. The amino acid sequences of selected fingers which bind the same triplet were compared to examine how sequence-specific DNA recognition occurs. The results can be rationalised in terms of coded interactions between zinc fingers and DNA, involving base contacts from a few α-helical positions.

An alternative to the rational but biased design of proteins with new specificities, is the isolation of desirable mutants from a large pool. A powerful method of selecting such proteins is the cloning of peptides (Smith 1985 Science 228, 1315–1317), or protein domains (McCafferty et al., 1990 Nature (London) 348, 552–554; Bass et al., 1990 Proteins 8, 309–314), as fusions to the minor coat protein (pIII) of bacteriophage fd, which leads to their expression on the tip of the capsid. Phage displaying the peptides of interest can then be affinity purified and amplified for use in further rounds of selection and for DNA sequencing of the cloned gene. The inventors applied this technology to the study of zinc finger-DNA interactions after demonstrating that functional zinc finger proteins can be displayed on the surface of fd phage, and that the engineered phage can be captured on a solid support coated with specific DNA. A phage display library was created comprising variants of the middle finger from the DNA binding domain of Zif268 (a mouse transcription factor containing 3 zinc fingers—Christy et al., 1988). DNA of fixed sequence was used to purify phage from this library over several rounds of selection, returning a number of different but related zinc fingers which bind the given DNA. By comparing similarities in the amino acid sequences of functionally equivalent fingers we deduce the likely mode of interaction of these fingers with DNA. Remarkably, it would appear that many base contacts can occur from three primary positions on the α-helix of the zinc finger, correlating (in hindsight) with the implications of the crystal structure of Zif268 bound to DNA (Pavletich & Pabo 1991). The ability to select or design zinc fingers with desired specificity means that DNA binding proteins containing zinc fingers can now be "made-to-measure".

MATERIALS AND METHODS

Construction and cloning of genes. The gene for the first three fingers (residues 3–101) of Transcription Factor IIIA (TFIIIA) was amplified by PCR from the cDNA clone of TFIIIA using forward and backward primers which contain restriction sites for NotI and SfiI respectively. The gene for the Zif268 fingers (residues 333–420) was assembled from 8 overlapping synthetic oligonucleotides, giving SfiI and NotI overhangs. The genes for fingers of the phage library were synthesised from 4 oligonucleotides by directional end to end ligation using 3 short complementary linkers, and amplified by PCR from the single strand using forward and backward primers which contained sites for NotI and SfiI respectively. Backward PCR primers in addition introduced Met-Ala-Glu as the first three amino acids of the zinc finger peptides, and these were followed by the residues of the wild type or library fingers as discussed in the text. Cloning overhangs were produced by digestion with SfiI and NotI where necessary. Fragments were ligated to 1 µg similarly prepared Fd-Tet-SN vector. This is a derivative of fd-tet-DOG1 (Hoogenboom et al., 1991 Nucleic Acids Res. 19, 4133–4137) in which a section of the pelB leader and a restriction site for the enzyme SfiI (underlined) have been added by site-directed mutagenesis using the oligonucleotide (Seq ID No. 1):

```
5' CTCCTGCAGTTGGACCTGTGCCATGGCCG
GCTGGGCCGCATAGAATGGAACAACTAAAGC 3'
``` which anneals in the region of the polylinker, (L. Jespers, personal communication). Electrocompetent DH5α cells were transformed with recombinant vector in 200 ng aliquots, grown for 1 hour in 2×TY medium with 1% glucose, and plated on TYE containing 15 µg/ml tetracycline and 1% glucose.

Figure 2:
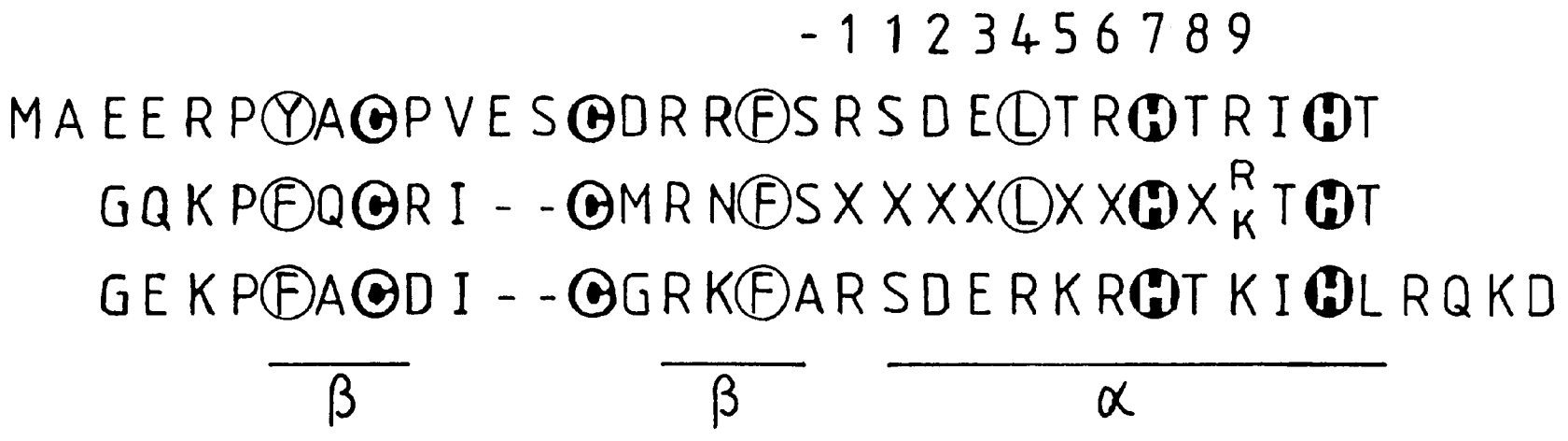

FIG. 2 shows the amino acid sequence (Seq ID No. 2) of the three zinc fingers from Zif268 used in the phage display library. The top and bottom rows represent the sequence of the first and third fingers respectively. The middle row represents the sequence of the middle finger. The randomised positions in the α-helix of the middle finger have residues marked 'X'. The amino acid positions are numbered relative to the first helical residue (position 1). For amino acids at positions −1 to +8, excluding the conserved Leu and His, codons are equal mixtures of (G,A,C)NN: T in the first base position is omitted in order to avoid stop codons, but this has the unfortunate effect that the codons for Trp, Phe, Tyr and Cys are not represented. Position +9 is specified by the codon A(G,A)G, allowing either Arg or Lys. Residues of the hydrophobic core are circled, whereas the zinc ligands are written as white letters on black circles. The positions forming the β-sheets and the α-helix of the zinc fingers are marked below the sequence.

Phage selection. Colonies were transferred from plates to 200 ml 2×TY/Zn/Tet (2×TY containing 50 µM Zn(CH3.C00)$_2$ and 15 µg/ml tetracycline) and grown overnight. Phage were purified from the culture supernatant by two rounds of precipitation using 0.2 volumes of 20% PEG/2.5M NaCl containing 50 µM Zn(CH3.C00)$_2$, and resuspended in zinc finger phage buffer (20 mM HEPES pH7.5, 50 mM NaCl, 1 mM MgCl$_2$ and 50 µM Zn(CH3.COO)$_2$). Streptavidin-coated paramagnetic beads (Dynal) were washed in zinc finger phage buffer and blocked for 1 hour at room temperature with the same buffer made up to 6% in fat-free dried milk (Marvel). Selection of phage was over three rounds: in the first round, beads (1 mg) were saturated with biotinylated oligonucleotide (~80 nM) and then washed prior to phage binding, but in the second and third rounds 1.7 nM oligonucleotide and 5 µg poly dGC (Sigma) were added to the beads with the phage. Binding reactions (1.5 ml) for 1 hour at 15° C. were in zinc finger phage buffer made up to 2% in fat-free dried milk (Marvel) and 1% in Tween 20, and typically contained 5×10$^{11}$ phage. Beads were washed 15 times with 1 ml of the same buffer. Phage were eluted by shaking in 0.1M triethylamine for 5 min and neutralised with an equal volume of 1M Tris pH7.4. Log phase E. coli TG1 in 2×TY were infected with eluted phage for 30 min at 37° C. and plated as described above. Phage titres were determined by plating serial dilutions of the infected bacteria.

The phage selection procedure, based on affinity purification, is illustrated schematically in FIG. 1: zinc fingers (A) are expressed on the surface of fd phage(B) as fusions to the the minor coat protein (C). The third finger is mainly obscured by the DNA helix. Zinc finger phage are bound to 5'-biotinylated DNA oligonucleotide [D] attached to streptavidin-coated paramagnetic beads [E], and captured using a magnet [F]. (Figure adapted from Dynal A. S. and also Marks et al. (1992 J. Biol. Chem. 267, 16007–16105).

Figure 3:
FIG. 3 shows the DNA sequences of three oligonucleotides (Seq ID No.s 3–8) used in the affinity purification of phage display particles.
Figure 5A:
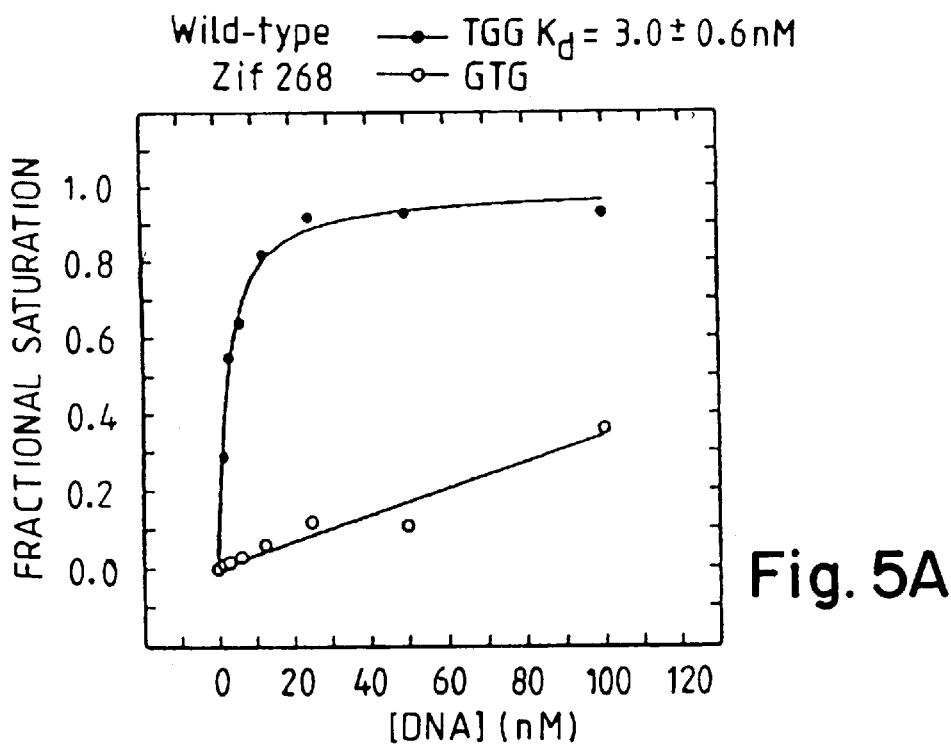
FIGS. 5A–5F show three of fractional saturation against concentration of DNA (nM) for various binding motifs and target DNA triplets.
Figure 5B:
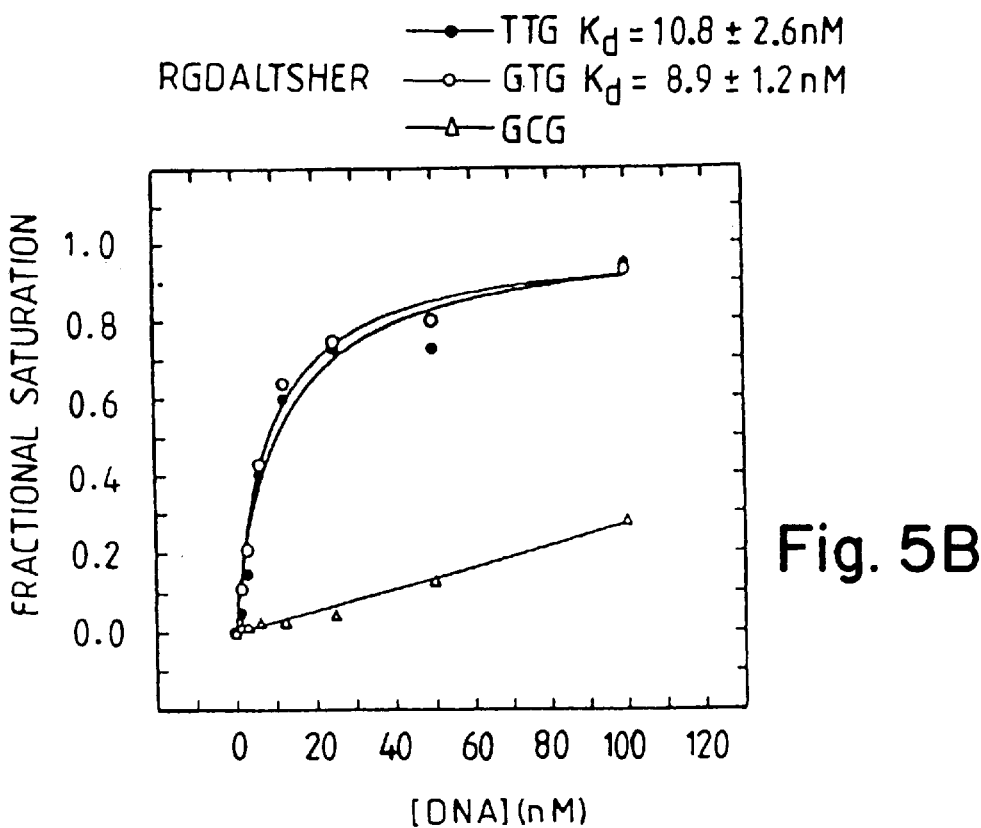
Figure 5C:
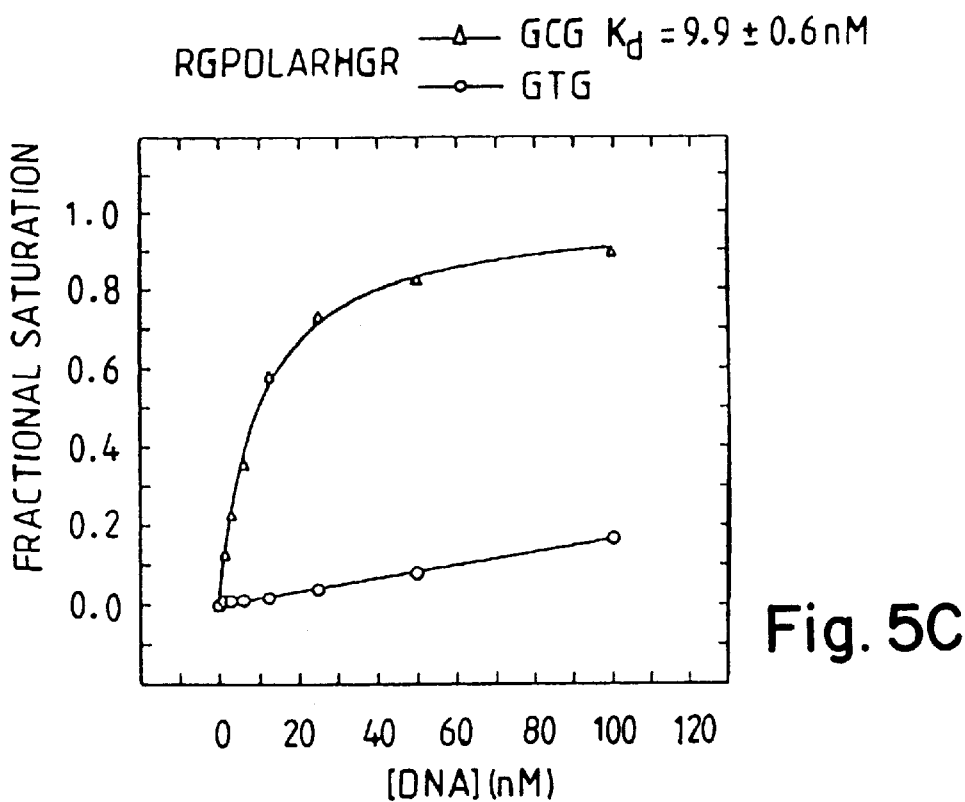
Figure 5D:
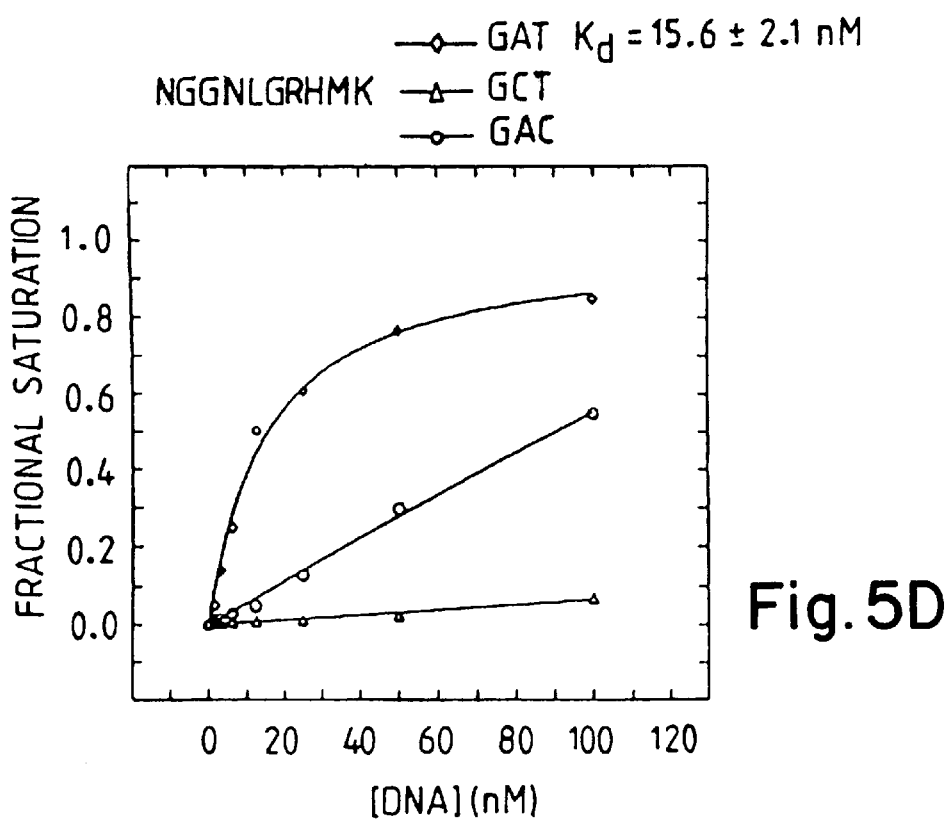
Figure 5E:
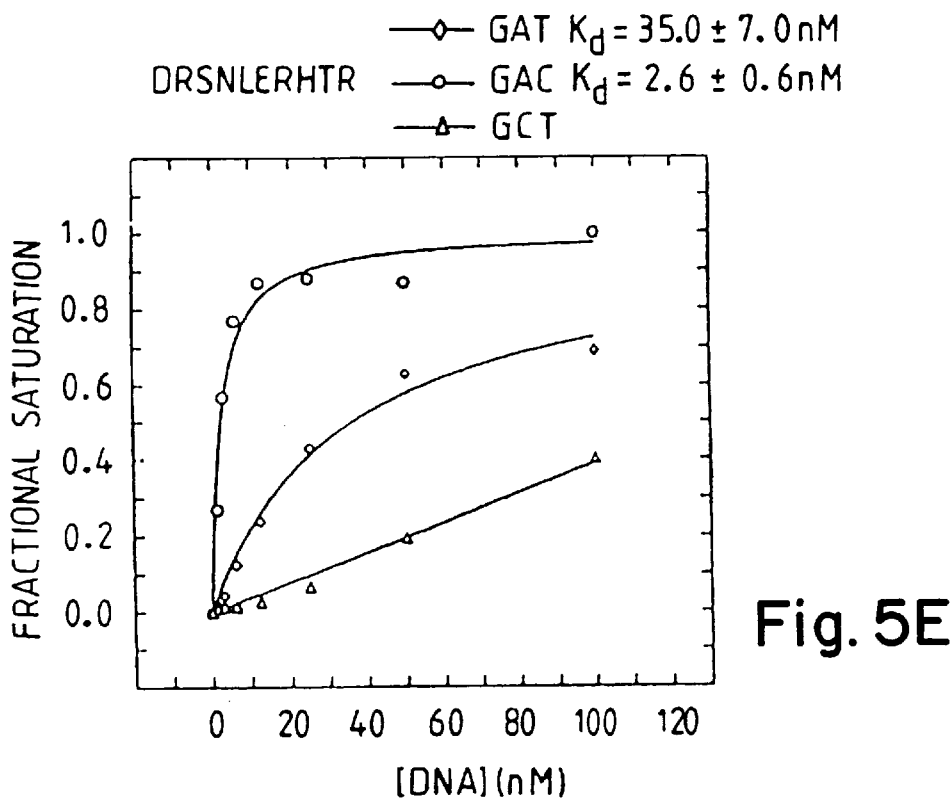
Figure 5F:
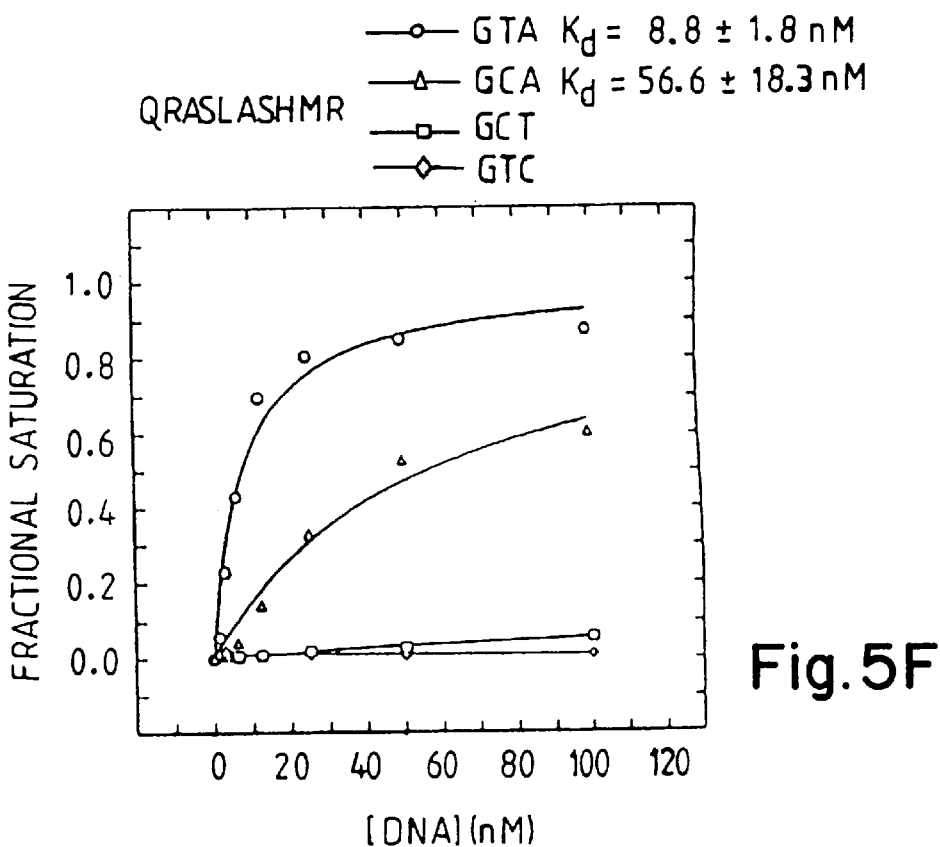

FIG. 3 shows sequences (Seq ID No.s 3–8) of DNA oligonucleotides used to purify (i) phage displaying the first three fingers of TFIIIA, (ii) phage displaying the three fingers of Zif268, and (iii) zinc finger phage from the phage display library. The Zif268 consensus operator sequence used in the X-ray crystal structure (Pavletich & Pabo 1991 Science 252, 809–817) is highlighted in (ii), and in (iii) where "X" denotes a base change from the ideal operator in oligonucleotides used to purify phage with new specificities. Biotinylation of one strand is shown by a circled "B".

Sequencing of selected phage. Single colonies of transformants obtained after three rounds of selection as described, were grown overnight in 2×TY/Zn/Tet. Small aliquots of the cultures were stored in 15% glycerol at −20° C., to be used as an archive. Single-stranded DNA was prepared from phage in the culture supernatant and sequenced using the modified T7 RNA polymerase SEQUENASE™ 2.0 kit (U.S. Biochemical Corp.).

RESULTS AND DISCUSSION

Phage display of 3-finger DNA-Binding Domains from TFIII or Zif268. Prior to the construction of a phage display library, the inventors demonstrated that peptides containing three fully functional zinc fingers could be displayed on the surface of viable fd phage when cloned in the vector Fd-Tet-SN. In preliminary experiments, the inventors cloned as fusions to pIII firstly the three N-terminal fingers from TFIIIA (Ginsberg et al., 1984 Cell 39, 479–489), and secondly the three fingers from Zif-268 (Christy et al., 1988), for both of which the DNA binding sites are known. Peptide fused to the minor coat protein was detected in Western blots using an anti-pIII antibody (Stengele et al., 1990 J. Mol. Biol. 212, 143–149). Approximately 10–20% of total pIII in phage preparations was present as fusion protein.

Phage displaying either set of fingers were capable of binding to specific DNA oligonucleotides, indicating that zinc fingers were expressed and correctly folded in both instances. Paramagnetic beads coated with specific oligonucleotide were used as a medium on which to capture DNA-binding phage, and were consistently able to return between 100 and 500-fold more such phage, compared to free beads or beads coated with non-specific DNA. Alternatively, when phage displaying the three fingers of Zif268 were diluted 1:1.7×10$^3$ with Fd-Tet-SN phage not bearing zinc fingers, and the mixture incubated with beads coated with Zif-268 operator DNA, one in three of the total phage eluted and transfected into *E. coli* were shown by colony hybridisation to carry the Zif268 gene, indicating an enrichment factor of over 500 for the zinc finger phage. Hence it is clear that zinc fingers displayed on fd phage are capable of preferential binding to DNA sequences with which they can form specific complexes, making possible the enrichment of wanted phage by factors of up to 500 in a single affinity purification step. Therefore, over multiple rounds of selection and amplification, very rare clones capable of sequence-specific DNA binding, can be selected from a large library.

A phage display library of zinc fingers from Zif268. The inventors have made a phage display library of the three fingers of Zif268 in which selected residues in the middle finger are randomised (FIG. 2), and have isolated phage bearing zinc fingers with desired specificity using a modified Zif268 operator sequence (Christy & Nathans 1989 Proc. Natl. Acad. Sci. USA 86, 8737–8741) in which the middle DNA triplet is altered to the sequence of interest (FIG. 3). In order to be able to study both the primary and secondary putative base recognition positions which are suggested by database analysis (Jacobs 1992 EMBO J. 11, 4507–4517), the inventors have designed the library of the middle finger so that, relative to the first residue in the α-helix (position +1), positions −1 to +8, but excluding the conserved Leu and His, can be any amino acid except Phe, Tyr, Trp and Cys which occur only rarely at those positions (Jacobs 1993 Ph.D. thesis, University of Cambridge). In addition, the inventors have allowed position +9 (which might make an inter-finger contact with Ser at position −2 (Pavletich & Pabo 1991)) to be either Arg or Lys, the two most frequently occurring residues at that position.

The logic of this protocol, based upon the Zif268 crystal structure (Pavletich & Pabo 1991), is that the randomised finger is directed to the central triplet since the overall register of protein-DNA contacts is fixed by its two neighbours. This allows the examination of which amino acids in the randomised finger are the most important in forming specific complexes with DNA of known sequence. Since comprehensive variations are programmed in all the putative contact positions of the α-helix, it is possible to conduct an objective study of the importance of each position in DNA-binding (Jacobs 1992).

The size of the phage display library required, assuming full degeneracy of the 8 variable positions, is $(16^7 \times 2^1) = 5.4 \times 10^8$, but because of practical limitations in the efficiency of transformation with Fd-Tet-SN, the inventors were able to clone only 2.6×10$^6$ of these. The library used is therefore some two hundred times smaller than the theoretical size necessary to cover all the possible variations of the α-helix. Despite this shortfall, it has been possible to isolate phage which bind with high affinity and specificity to given DNA sequences, demonstrating the remarkable versatility of the zinc finger motif. Amino acid-base contacts in zinc finger-DNA complexes deduced from phage display selection. Of the 64 base triplets that could possibly form the binding site for variations of finger 2, the inventors have so far used 32 in attempts to isolate zinc finger phage as described. Results from these selections are shown in Table 1, which lists amino acid sequences (Seq ID No.s 52–118) of the variant α-helical regions from clones of library phage selected after 3 rounds of screening with variants of the Zif268 operator.

TABLE 1

|   |     |     | -1123456789 |
|---|-----|-----|-------------|
| a | CAG | 1   | RGDHLKDHIK  |
|   |     | 9   | RSDHLTTHIR  |
| b | TGA | 3   | QLAHLSTHKR  |
|   |     | 1   | QSVHLQSHSR  |
|   |     | (3) | QKGHLTEHRK  |
| c | GAA | 2   | QGGNLVRHLR  |
|   |     | 1   | NGGNLGRHMK  |
|   |     | 1   | ARSNLLRHTR  |
|   |     | 2   | LQSNLYRHQR  |
|   |     | 1   | IASNLLRHQR  |
| d | GAT | 1   | DRSNLERHTR  |
|   |     | 1   | NQSNLERHHR  |
|   |     | 1   | QQSNLVRHQR  |
|   |     | 1   | NGGNLGRHMK  |
|   |     | 1   | NGANLERHRR  |
|   |     | 1   | SQGNLQRHGR  |
|   |     | 1   | SHPNLNRHLK  |
|   |     | 1   | IPGNLTRHGR  |
| e | GAC | 4   | DRSNLERHTR  |
|   |     | 1   | DHANLARHTR  |

TABLE 1-continued

| | | | |
|---|---|---|---|
| f | GCC | 2 | QRSSLTRHTR |
| | | 7 | ERGTLARHEK |
| | | 1 | QRRLLDRHQR |
| g | GTC | 6 | QRSSLTRHTR |
| | | 1 | ERTSLSRHIR |
| h | GCA | 1 | SAGTLVRHSK |
| | | 2 | QAQTLQRHLK |
| | | 2 | EKATLARHMK |
| | | 1 | TGGSLARHER |
| i | GCT | 1 | HQSTLGRHTR |
| | | 1 | EKATLARHMK |
| | | 1 | QAQTLQRHLK |
| | | 1 | ERGTLARHEK |
| | | 1 | QRDALARHQK |
| | | 1 | RGPDLARHGR |
| | | 1 | SRDVLRRHNR |
| j | ACG | 8 | RRDYLMNHIR |
| | | 1 | RKDYLYSHVR |
| k | ATG | 8 | RRDYLMNHIR |
| | | 1 | SGDALTSHER |
| | | 1 | SVDALEAHRR |
| l | GTA | 1 | QRSSLTRHTR |
| | | 1 | ERTSLSRHIR |
| | | (1) | QARSLTRHQR |
| | | (2) | TGGSLARHER |
| | | 2 | QRASLARHMR |
| | | 1 | NRDTLTRHSK |
| | | (1) | ERGTLARHER |
| m | TTG | 9 | SGDALTSHER |
| | | 1 | RADALMVHKR |
| n | CCG | 5 | RQDTLVGHER |
| | | 1 | RQSTLVRHTR |
| | | 2 | RAADLNRHVR |
| | | 1 | RKDYLVSHVR |
| | | 1 | RRDYLMNHIR |
| o | GCG | 1 | SSDTLKRHGK |
| | | 3 | SGPQLARHGR |
| | | 1 | ARETLQRHTR |
| | | 3 | REDYLIRHGK |
| | | 1 | QSDLLQRHHK |
| p | GTG | 1 | RLDGLRTHLK |
| | | 1 | SGDALTSHER |
| | | 1 | RADALMVHKR |
| | | 1 | SVDALEAHRR |
| | | 1 | RRDYLLNHIR |
| | | 2 | REDYLIRHGK |
| | | 1 | SSDLLQRHHK |

In Table 1, the amino acid sequences, aligned in the one letter code, are listed alongside the DNA oligonucleotides (a to p) used in their purification. The latter are denoted by the sequence of the central DNA triplet in the "bound" strand of the variant Zif268 operator. The amino acid positions are numbered relative to the first helical residue (position 1), and the three primary recognition positions are highlighted. The accompanying numbers indicate the independent occurrences of that clone in the sequenced population (5–10 colonies); where numbers are in parentheses, the clone(s) were detected in the penultimate round of selection but not in the final round. In addition to the DNA triplets shown here, others were also used in attempts to select zinc finger phage from the library, but most selected two clones, one having the α-helical sequence KASNLVSHIR (Seq ID No. 119), and the other having the sequence LRHNLETHMR (Seq ID No. 120). Those triplets were: ACT, AAA, TTT, CCT, CTT, TTC, AGT, CGA, CAT, AGA, AGC and AAT.

In general the inventors have been unable to select zinc fingers which bind specifically to triplets without a 5' or 3' guanine, all of which return the same limited set of phase after three rounds of selection (see). However for each of the other triplets used to screen the library, a family of zinc finger phage is recovered. In these families is found a sequence bias in the randomised α-helix, which is interpreted as revealing the position and identity of amino acids used to contact the DNA. For instance: the middle fingers from the 8 different clones selected with the triplet GAT (Table 1d) all have Asn at position +3 and Arg at position +6, just as does the first zinc finger of the Drosophila protein tramtrack in which they are seen making contacts to the same triplet in the cocrystal with specific DNA (Fairall et al., 1993). This indicates that the positional recurrence of a particular amino acid in functionally equivalent fingers is unlikely to be coincidental, but rather because it has a functional role. Thus using data collected from the phage display library (Table 1) it is possible to infer most of the specific amino acid-DNA interactions. Remarkably, most of the results can be rationalised in terms of contacts from the three primary α-helical positions (−1, +3 and +6) identified by X-ray crystallography (Pavletich & Pabo 1991) and database analysis (Jacobs 1992).

As has been pointed out before (Berg 1992 Proc. Natl Acad. Sci. USA 89, 11109–11110), guanine has a particularly important role in zinc finger-DNA interactions. When present at the 5' (e.g. Table 1c-i) or 3' (e.g. Table 1m-o) end of a triplet, G selects fingers with Arg at position +6 or −1 of the α-helix respectively. When G is present in the middle position of a triplet (e.g. Table 1b), the preferred amino acid at position +3 is His. Occasionally, G at the 5' end of a triplet selects Ser or Thr at +6 (e.g. Table 1p). Since G can only be specified absolutely by Arg (Seeman et al., 1976 Proc. Nat. Acad. Sci. USA 73, 804–808), this is the most common determinant at −1 and +6. One can expect this type of contact to be a bidentate hydrogen bonding interaction as seen in the crystal structures of Zif268 (Pavletich & Pabo 1991 Science 252, 809–817) and tramtrack (Fairall et al., 1993). In these structures, and in almost all of the selected fingers in which Arg recognises G at the 3' end, Asp occurs at position +2 to buttress the long Arg side chain (e.g. Table 1o,p). When position −1 is not Arg, Asp rarely occurs at +2, suggesting that in this case any other contacts it might make with the second DNA strand do not contribute significantly to the stability the protein-DNA complex.

Adenine is also an important determinant of sequence specificity, recognised almost exclusively by Asn or Gln which again are able to make bidentate contacts (Seeman et al., 1976). When A is present at the 3' end of a triplet, Gln is often selected at position −1 of the α-helix, accompanied by small aliphatic residues at +2 (e.g. Table 1b). Adenine in the middle of the triplet strongly selects Asn at +3 (e.g. Table 1c-e), except in the triplet CAG (Table 1a) which selected only two types of finger, both with His at +3 (one being the wild-type Zif268 which contaminated the library during this experiment). The triplets ACG (Table 1j) and ATG (Table 1k), which have A at the 5' end, also returned oligoclonal mixtures of phage, the majority of which were of one clone with Asn at +6.

In theory, cytosine and thymine cannot reliably be discriminated by a hydrogen bonding amino acid side chain in the major groove (Seeman et al., 1976). Nevertheless, C in the 3' position of a triplet shows a marked preference for Asp or Glu at position −1, together with Arg at +1 (e.g. Table 1e-g). Asp is also sometimes selected at +3 and +6 when C is in the middle (e.g. Table 1o) and 5' (e.g. Table 1a) position respectively. Although Asp can accept a hydrogen bond from the amino group of C, one should note that the positive molecular charge of C in the major groove (Hunter 1993 J. Mol. Biol. 230, 1025–1054) will favour an interaction with Asp regardless of hydrogen bonding contacts. However, C in the middle position most frequently selects Thr (e.g. Table 1i), Val or Leu (e.g. Table 1o) at +3. Similarly, T in the middle position most often selects Ser (e.g. Table 1i), Ala or Val (e.g. Table 1p) at +3. The aliphatic amino acids are unable to make hydrogen bonds but Ala probably has a hydrophobic interaction with the methyl group of T, whereas a longer side chain such as Leu can exclude T and pack against the ring of C. When T is at the 5' end of a triplet, Ser and Thr are selected at +6 (as is occasionally the case for G at the 5' end). Thymine at the 3' end of a triplet selects a variety of polar amino acids at −1 (e.g. Table 1d), and occasionally returns fingers with Ser at +2 (e.g. Table 1a) which could make a contact as seen in the traintrack crystal structure (Fairall et al., 1993).

Limitations of phage display. From Table 1 it can be seen that a consensus or bias usually occurs in two of the three primary positions (−1, +3 and +6) for any family of equivalent fingers, suggesting that in many cases phage selection is by virtue of only two base contacts per finger, as is observed in the Zif268 crystal structure (avletich & Pabo 1991). Accordingly, identical finger sequences are often returned by DNA sequences differing by one base in the central triplet. One reason for this is that the phage display selection, being essentially purification by affinity, can yield zinc fingers which bind equally tightly to a number of DNA triplets and so are unable to discriminate. Secondly, since complex formation is governed by the law of mass action, affinity selection can favour those clones whose representation in the library is greatest even though their true affinity for DNA is less than that of other clones less abundant in the library. Phage display selection by affinity is therefore of limited value in distinguishing between permissive and specific interactions beyond those base contacts necessary to stabilise the complex. Thus in the absence of competition from fingers which are able to bind specifically to a given DNA, the tightest non-specific complexes will be selected from the phage library. Consequently, results obtained by phage display selection from a library must be confirmed by specificity assays, particularly when that library is of limited size.

Conclusion. The amino acid sequence biases observed within a family of functionally equivalent zinc fingers indicate that, of the a-helical positions randomised in this study, only three primary (−1, +3 and +6) and one auxiliary (+2) positions are involved in recognition of DNA. Moreover, a limited set of amino acids are to be found at those positions, and it is presumed that these make contacts to bases. The indications therefore are that a code can be derived to describe zinc finger-DNA interactions. At this stage however, although sequence homologies are strongly suggestive of amino acid preferences for particular basepairs, one cannot confidently deduce such rules until the specificity of individual fingers for DNA triplets is confirmed. The inventors therefore defer making a summary table of these preferences until the following example, in which is described how randomised DNA binding sites can be used to this end.

While this work was in progress, a paper by Rebar and Pabo was published (Rebar & Pabo 1994 Science 263, 671–673) in which phage display was also used to select zinc fingers with new DNA-binding specificities. These authors constructed a library in which the first finger of Zif268 is randomised, and screened with tetranucleotides to take into account end effects such as additional contacts from variants of this finger. Only 4 positions (−1, +2, +3 and +6) were randomised, chosen on the basis of the earlier X-ray crystal structures. The results presented above, in which more positions were randomised, to some extent justifies Rebar and Pabo's use of the four random positions without apparent loss of effect, although further selections may reveal that the library is compromised. However, randomising only four positions decreases the theoretical library size so that full degeneracy can be achieved in practice. Nevertheless the inventors found that the results obtained by Rebar and Pabo by screening their complete library with two variant Zif268 operators, are in agreement with their conclusions derived from an incomplete library. On the one hand this again highlights the versatility of zinc fingers but, remarkably, so far both studies have been unable to produce fingers which bind to the sequence CCT. It will be interesting to see whether sequence biases such as we have detected would be revealed, if more selections were performed using Rebar and Pabo's library. In any case, it would be desirable to investigate the effects on selections of using different numbers of randomised positions in more complete libraries than have been used so far.

The original position or context of the randomised finger in the phage display library might bear on the efficacy of selected fingers when incorporated into a new DNA-binding domain. Selections from a library of the outer fingers of a three finger peptide (Rebar & Pabo, 1994 Science 263, 671–673; Jamieson et al., 1994 Biochemistry 33, 5689–5695) are capable of producing fingers which bind DNA in various different modes, while selections from a library of the middle finger should produce motifs which are more constrained. Accordingly, Rebar and Pabo do not assume that the first finger of Zif268 will always bind a triplet, and screened with a tetranucleotide binding site to allow for different binding modes. Thus motifs selected from libraries of the outer fingers might prove less amenable to the assembly of multifinger proteins, since binding of these fingers could be perturbed on constraining them to a particular binding mode, as would be the case for fingers which had to occupy the middle position of an assembled three-finger protein. In contrast, motifs selected from libraries of the middle finger, having been originally constrained, will presumably be able to preserve their mode of binding even when placed in the outer positions of an assembled DNA-binding domain.

FIGS. 10A–10C show different strategies for the design of tailored zinc finger proteins. (A) A three-finger DNA-binding motif is selected en bloc from a library of three randomised fingers. (B) A three-finger DNA-binding motif is assembled out of independently selected fingers from a library of one randomised finger (e.g. the middle finger of Zif268). (C) A three-finger DNA-binding motif is assembled out of independently selected fingers from three positionally specified libraries of randomised zinc fingers.

Figure 11:
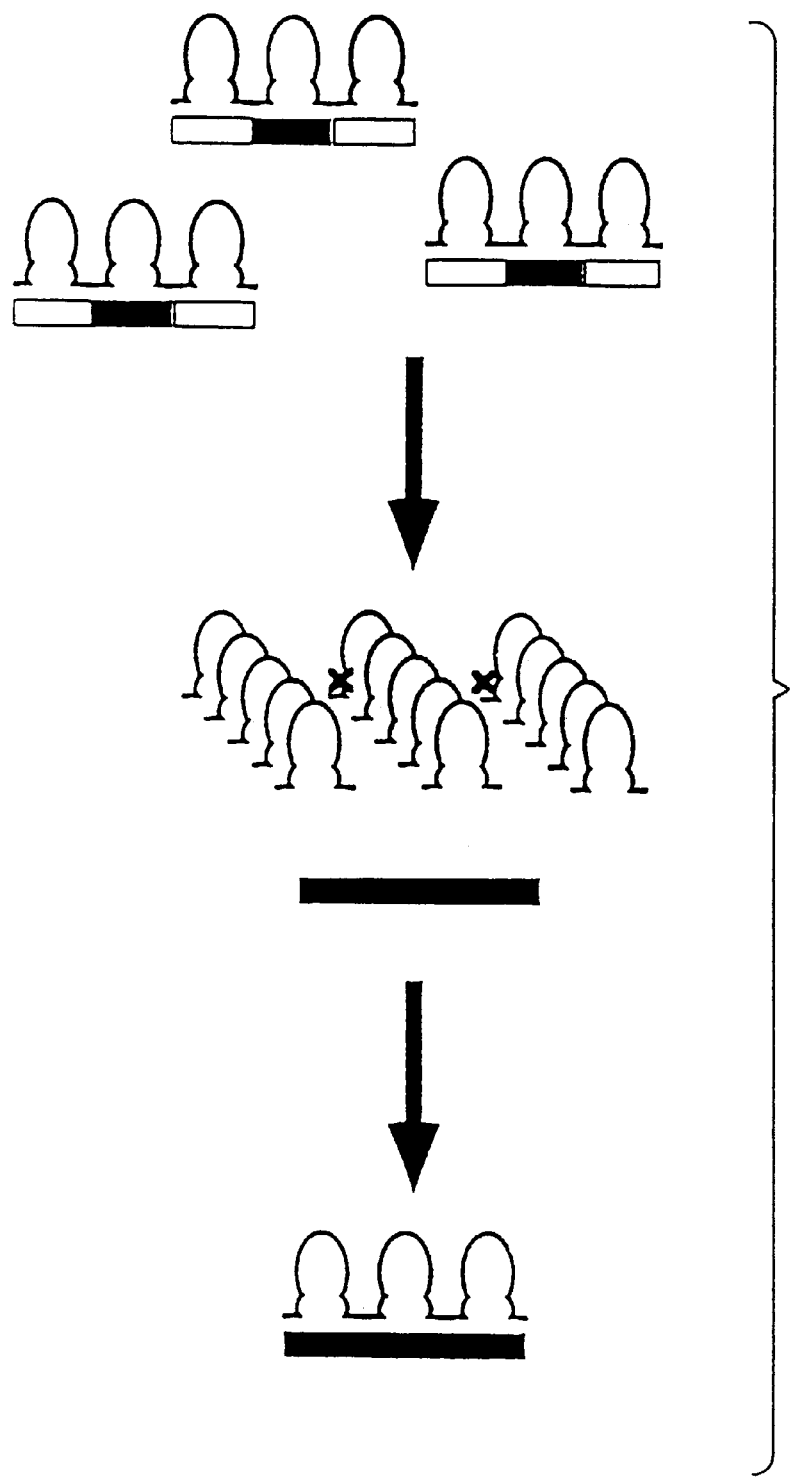

FIG. 11 illustrates the strategy of combinatorial assembly followed by en bloc selection. Groups of triplet-specific zinc fingers (A) isolated by phage display selection are assembled in random combinations and re-displayed on phage (B). A full-length target site (C) is used to select en bloc the most favourable combination of fingers (D).

EXAMPLE 2

This example describes a new technique to deal efficiently with the selection of a DNA binding site for a given zinc finger (essentially the converse of example 1). This is desirable as a safeguard against spurious selections based on the screening of display libraries. This may be done by screening against libraries of DNA triplet binding sites randomised in two positions but having one base fixed in the third position. The technique is applied here to determine the specificity of fingers previously selected by phage display. The inventors found that some of these fingers are able to specify a unique base in each position of the cognate triplet. This is further illustrated by examples of fingers which can discriminate between closely related triplets as measured by their respective equilibrium dissociation constants. Comparing the amino acid sequences of fingers which specify a particular base in a triplet, we infer that in most instances, sequence specific binding of zinc fingers to DNA can be achieved using a small set of amino acid-base contacts amenable to a code.

One can determine the optimal binding sites of these (and other) proteins, by selection from libraries of randomised DNA. This approach, the principle of which is essentially the converse of zinc finger phage display, would provide an equally informative database from which the same rules can be independently deduced. However until now, the favoured method for binding site determination (involving iterative selection and amplification of target DNA followed by sequencing), has been a laborious process not conveniently applicable to the analysis of a large database (Thiesen & Bach 1990 Nucleic Acids Res. 18. 3203–3209; Pollock & Treisman 1990 Nucleic Acids Res. 18, 6197–6204).

This example presents a convenient and rapid new method which can reveal the optimal binding site(s) of a DNA binding protein by single step selection from small libraries and use this to check the binding site preferences of those zinc fingers selected previously by phage display. For this application, the inventors have used 12 different mini-libraries of the Zif268 binding site, each one with the central triplet having one position defined with a particular base pair and the other two positions randomised. Each library therefore comprises 16 oligonucleotides and offers a number of potential binding sites to the middle finger, provided that the latter can tolerate the defined base pair. Each zinc finger phage is screened against all 12 libraries individually immobilised in wells of a microtitre plate, and binding is detected by an enzyme immunoassay. Thus a pattern of acceptable bases at each position is disclosed, which the inventors term a "binding site signature". The information contained in a binding site signature encompasses the repertoire of binding sites recognised by a zinc finger.

The binding site signatures obtained, using zinc finger phage selected as described in example 1, reveal that the selection has yielded some highly sequence-specific zinc finger binding motifs which discriminate at all three positions of a triplet. From measurements of equilibrium dissociation constants it is found that these fingers bind tightly to the triplets indicated in their signatures, and discriminate against closely related sites (usually by at least a factor of ten). The binding site signatures allow progress towards a specificity code for the interactions of zinc fingers with DNA.

MATERIALS AND METHODS

Binding site signatures. Flexible flat-bottomed 96-well microtitre plates (Falcon) were coated overnight at 4° C. with streptavidin (0.1 mg/ml in 0.1M $NaHCO_3$ pH8.6, 0.3% $NaN_3$). Wells were blocked for one hour with PBS/Zn (PBS, 50 $\mu$M Zn $(CH3.COO)_2$) containing 2% fat-free dried milk (Marvel), washed 3 times with PBS/Zn containing 0.1% TWEEN, and another 3 times with PBS/Zn. The "bound" strand of each oligonucleotide library was made synthetically and the other strand extended from a 5'-biotinylated universal primer using DNA polymerase I (Klenow fragment). Fill-in reactions were added to wells (0.8 pmole DNA library in each) in PBS/Zn for 15 minutes, then washed once with PBS/Zn containing 0.1% TWEEN, and once again with PBS/Zn. Overnight bacterial cultures each containing a selected zinc finger phage were grown in 2×TY containing 50 mM $Zn(CH3.C00)_2$ and 15 $\mu$g/ml tetracycline at 30° C. Culture supernatants containing phage were diluted tenfold by the addition of PBS/Zn containing 2% fat-free dried milk (Marvel), 1% TWEEN and 20 $\mu$g/ml sonicated salmon sperm DNA. Diluted phage solutions (50 $\mu$l) were applied to wells and binding, allowed to proceed for one hour at 20° C. Unbound phage were removed by washing 5 times with PBS/Zn containing 1% TWEEN, and then 3 times with PBS/Zn. Bound phage were detected as described previously (Griffiths et al., 1994 EMBO J. In press), or using HRP-conjugated anti-M13 IgG (Pharmacia), and quantitated using SOFTMAX 2.32 (Molecular Devices Corp).

Figure 4:
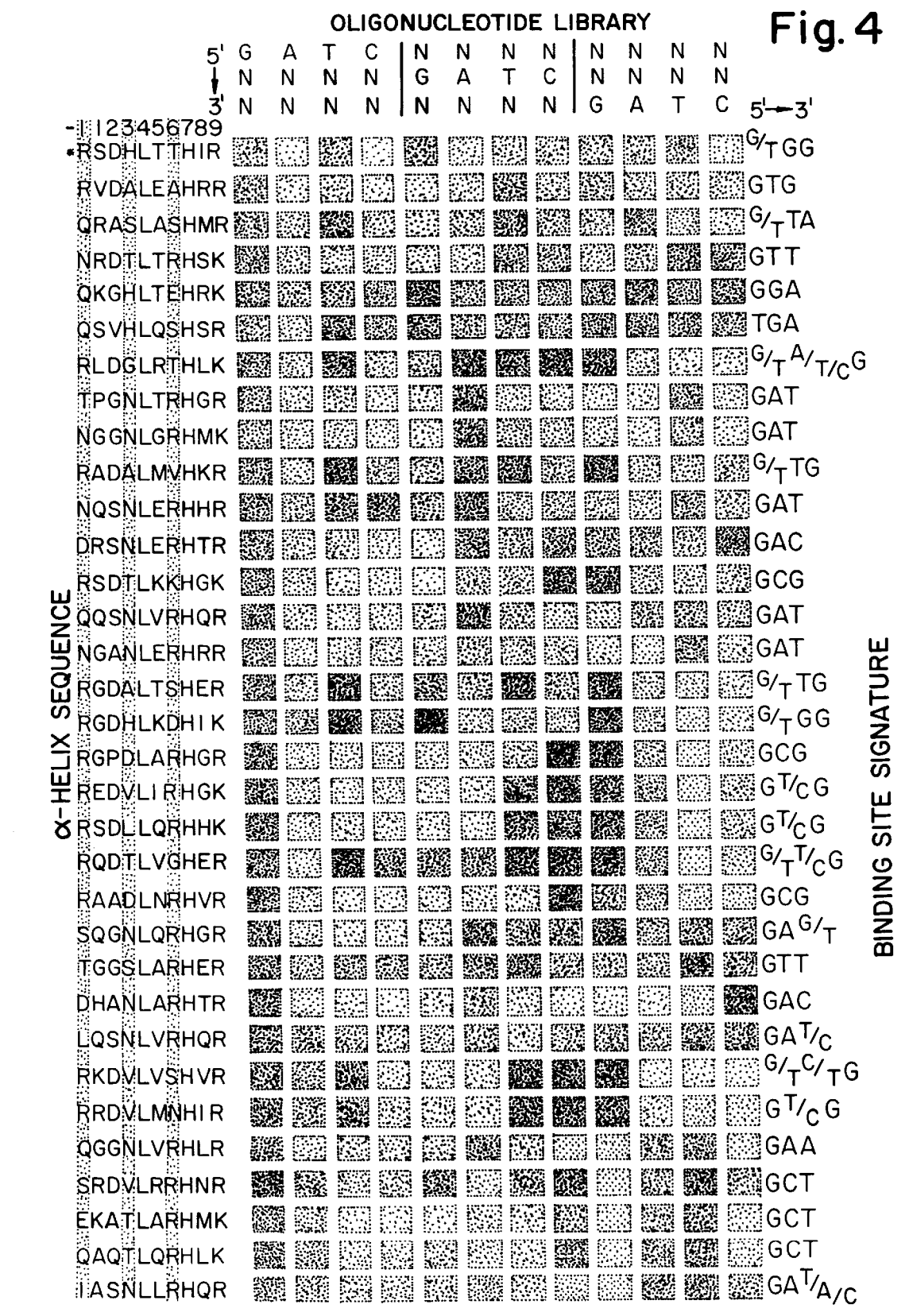

The results are shown in FIG. 4, which gives the binding site signatures of individual zinc finger phage The figure represents binding of zinc finger phage to randomised DNA immobilised in the wells of microtitre plates. To test each zinc finger phage against each oligonucleotide library (see above), DNA libraries are applied to columns of wells (down the plate), while rows of wells (across the plate) contain equal volumes of a solution of a zinc finger phage. The identity of each library is given as the middle triplet of the "bound" strand of Zif268 operator, where N represents a mixture of all 4 nucleotides. The zinc finger phage is specified by the sequence of the variable region of the middle finger, numbered relative to the first helical residue (position 1), and the three primary recognition positions are highlighted. Bound phage are detected by an enzyme immunoassay. The approximate strength of binding is indicated by a grey scale proportional to the enzyme activity. From the pattern of binding to DNA libraries, called the "signature" of each clone, one or a small number of binding sites can be read off and these are written on the right of the figure.

Determination of apparent equilibrium dissociation constants. Overnight bacterial cultures were grown in 2×TY/Zn/Tet at 30° C. Culture supernatants containing phage were diluted twofold by the addition of PBS/Zn containing 4% fat-free dried milk (Marvel), 2% Tween and 40 $\mu$g/ml sonicated salmon sperm DNA. Binding reactions, containing appropriate concentrations of specific 5'-biotinylated DNA and equal volumes of zinc finger phage solution, were allowed to equilibrate for 1 h at 20° C. All DNA was captured on streptavidin-coated paramagnetic beads (500 $\mu$g per well) which were subsequently washed 6 times with PBS/Zn containing 1% Tween and then 3 times with PBS/Zn. Bound phage were detected using HRP-conjugated anti-M13 IgG (Pharmacia) and developed as described (Griffiths et al., 1994). Optical densities were quantitated using SOFTMAX 2.32 (Molecular Devices Corp).

The results are shown in FIGS. 5A–5F, which are series of graphs of fractional saturation against concentration of DNA (nM). The two outer fingers carry the native sequence, as do the the two cognate outer DNA triplets. The sequence of amino acids occupying helical positions −1 to +9 of the varied finger are shown in each case. The graphs show that the middle finger can discriminate closely related triplets, usually by a factor of ten. The graphs allowed the determination of apparent equilibrium dissociation constants, as below.

Estimations of the $K_d$ are by fitting to the equation $K_d=[DNA].[P]/[DNA.P]$, using the software package KALEIDAGRAPH™ Version 2.0 programme (Abelbeck Software). Owing to the sensitivity of the ELISA used to detect protein-DNA complex, the inventors were able to use zinc finger phage concentrations far below those of the DNA, as is required for accurate calculations of the $K_d$. The technique used here has the advantage that while the concentration of DNA (variable) must be known accurately, that of the zinc fingers (constant) need not be known (Choo & Kiug 1993 Nucleic Acids Res. 21, 3341–3346). This circumvents the problem of calculating the number of zinc finger peptides expressed on the tip of each phage, although since only 10–20% of the gene III protein (pIII) carries such peptides one would expect on average less than one copy per phage. Binding is performed in solution to prevent any effects caused by the avidity (Marks et al., 1992) of phage for DNA immobilised on a surface. Moreover, in this case measurements of $K_d$ by ELISA are made possible since equilibrium is reached in solution prior to capture on the solid phase.

RESULTS AND DISCUSSION

The binding site signature of the second finger of Zif268. The top row of FIG. 4 shows the signature of the second finger of wild type Zif268. From the pattern of strong signals indicating binding to oligonucleotide libraries having GNN, TNN, NGN and NNG as the middle triplet, it emerges that the optimal binding site for this finger is T/G,G,G, in accord with the published consensus sequence (Christy & Nathans 1989 Proc. Natl. Acad. Sc. USA 86, 8737–8741). This has implications for the interpretation of the X-ray crystal structure of Zif268 solved in complex with consensus operator having TGG as the middle triplet (Pavletich & Pabo 1991). For instance, His at position +3 of the middle finger was modelled as donating a hydrogen bond to N7 of G, suggesting an equivalent contact to be possible with N7 of A, but from the binding site signature we can see that there is discrimination against A. This implies that the His may prefer to make a hydrogen bond to O6 of G or a bifurcated hydrogen bond to both O6 and N7, or that a steric clash with the amino group of A may prevent a tight-interaction with this base. Thus by considering the stereochemistry of double helical DNA, binding site signatures can give insight into the details of zinc finger-DNA interactions.

Amino acid-base contacts in zinc finger-DNA complexes deduced from binding site signatures. The binding site signatures of other zinc fingers reveal that the phage selections performed in example 1 yielded highly sequence-specific DNA binding proteins. Some of these are able to specify a unique sequence for the middle triplet of a variant Zif268 binding site, and are therefore more specific than is Zif268 itself for its consensus site. Moreover, one can identify the fingers which recognise a particular oligonucleotide library, that is to say a specific base at a defined position, by looldng down the columns of FIG. 4. By comparing the amino acid sequences of these fingers one can identify any residues which have genuine preferences for particular bases on bound DNA. With a few exceptions, these are as previously predicted on the basis of phage display, and are summarised in Table 2.

Table 2 summarises frequently observed amino acid-base contacts in interactions of selected zinc fingers with DNA. The given contacts comprise a "syllabic" recognition code for appropriate triplets. Cognate amino acids and their positions in the α-helix are entered in a matrix relating each base to each position of a triplet. Auxiliary amino acids from position +2 can enhance or modulate specificity of amino acids at position −1 and these are listed as pairs. Ser or Thr at position +6 permit Asp +2 of the following finger (denoted Asp ++2) to specify both G and T indirectly, and the pairs are listed. The specificity of Ser+3 for T and Thr+3 for C may be interchangeable in rare instances while Val+3 appears to be consistently ambiguous.

TABLE 2

| | POSITION IN TRIPLET | | |
|---|---|---|---|
| | 5' | MIDDLE | 3' |
| G | Arg +6<br>Ser +6/Asp ++2<br>Thr +6/Asp ++2 | His +3 | Arg −1/Asp +2 |
| A | | Asn +3 | Gln −1/Ala +2 |
| T | Ser +6/Asp ++2<br>Thr +6/Asp ++2 | Ala +3<br>Ser +3<br>Val +3 | Asn −1<br>Gln −1/Ser +2 |
| C | | Asp +3<br>Leu +3<br>Thr +3<br>Val +3 | Asp −1 |

The binding site signatures also reveal an important feature of the phage display library which is important to the interpretation of the selection results. All the fingers in our panel, regardless of the amino acid present at position +6, are able to recognise G or both G and T at the 5' end of a triplet. The probable explanantion for this is that the 5' position of the middle triplet is fixed as either G or T by a contact from the invariant Asp at position +2 of finger 3 to the partner of either base on the complementary strand, analogous to those seen in the Zif268 (Pavletich & Pabo 1991 Science 252, 809–817) and tramtrack (Fairall et al., 1993) crystal structures (a contact to $NH_2$ of C or A respectively in the major groove). Therefore Asp at position +2 of finger 3 is dominant over the amino acid present at position +6 of the middle finger, precluding the possibility of recognition of A or C at the 5' position. Future libraries must be designed with this interaction omitted or the position varied. Interestingly, given the framework of the conserved regions of the three fingers, one can identify a rule in the second finger which specifies a frequent interaction with both G and T, viz the occurrence of Ser or Thr at position +6, which may donate a hydrogen bond to either base.

Modulation of base recognition by auxiliary positions. As noted above, position +2 is able to specify the base directly 3' of the 'cognate triplet', and can thus work in conjunction with position +6 of the preceding finger. The binding site signatures, whilst pointing to amino acid-base contacts from the three primary positions, indicate that auxiliary positions can play other parts in base recognition. A clear case in point is Gln at position −1, which is specific for A at the 3' end of a triplet when position +2 is a small non-polar amino acid such as Ala, though specific for T when polar residues such as Ser are at position +2. The strong correlation between Arg at position −1 and Asp at position +2, the basis of which is understood from the X-ray crystal structures of zinc fingers, is another instance of interplay between these two positions. Thus the amino acid at position +2 is able to modulate or enhance the specificity of the amino acid at other positions.

At position +3, a different type of modulation is seen in the case of Thr and Val which most often prefer C in the middle position of a triplet, but in some zinc fingers are able to recognise both C and T. This ambiguity occurs possibly as a result of different hydrophobic interactions involving the methyl groups of these residues, and here a flexibility in the inclination of the finger rather than an effect from another position per se may be the cause of ambiguous reading.

Quantitative measurements of dissociation constants. The binding site signature of a zinc finger reveals its differential base preferences at a given concentration of DNA. As the concentration of DNA is altered, one can expect the binding site signature of any clone to change, being more distinctive at low [DNA], and becoming less so at higher [DNA] as the $K_d$ of less favourable sites is approached and further bases become acceptable at each position of the triplet. Furthermore, because two base positions are randomly occupied in any one library of oligonucleotides, binding site signatures are not formally able to exclude the possibility of context dependence for some interactions. Therefore to supplement binding site signatures, which are essentially comparative, quantitative determinations of the equilibrium dissociation constant of each phage for different DNA binding sites are required. After phage display selection and binding site signatures, these are the third and definitive stage in assessing the specificity of zinc fingers.

Examples of such studies presented in FIGS. 5A–5F, which reveal that zinc finger phages bind the operators indicated in their binding site signatures with $K_d$s in the range of $10^{-8}$–$10^{-9}$M, and can discriminate against closely related binding sites by factors greater than an order of magnitude. Indeed FIG. 5 shows such differences in affinity for binding sites which differ in only one out of nine base pairs. Since the zinc fingers in our panel were selected from a library by non-competitive affinity purification, there is the possibility that fingers which are even more discriminatory can be isolated using a competitive selection process.

Measurements of dissociation constants allow different triplets to be ranked in order of preference according to the strength of binding. The examples here indicate that the contacts from either position −1 or +3 can contribute to discrimination. Also, the ambiguity in certain binding site signatures referred to above can be shown to have a basis in the equal affinity of certain figures for closely related triplets. This is demonstrated by the $K_d$s of the finger containing the amino acid sequence RGDALTSHER (Seq ID No. 100) for the triple TTG and GTG.

A code for zinc finger-DNA recognition. One would expect that the versatility of the zinc finger motif will have allowed evolution to develop various modes or binding to DNA (and even to RNA), which will be too diverse to fall under the scope of a single code. However, although a code may not apply to all zinc finger-DNA interactions, there is now convincing evidence that a code applies to a substantial subset. This code will fall short of being able to predict unfailingly the DNA binding site preference of any given zinc finger from its amino acid sequence, but may yet be sufficiently comprehensive to allow the design of zinc fingers with specificity for a given DNA sequence.

Using the selection methods of phage display (as described above) and of binding site signatures it is found that in the case of Zif268-like zinc fingers, DNA recognition involves four fixed principal (three primary and one auxiliary) positions on the α-helix, from where a limited and specific set of amino acid-base contacts result in recognition of a variety of DNA triplets. In other words, a code can describe the interactions of zinc fingers with DNA. Towards this code, one can propose amino acid-base contacts for almost all the entries in a matrix relating each base to each position of a triplet (Table 2). Where there is overlap, the results presented here complement those of Desjarlais and Berg who have derived similar rules by altering zinc finger specificity using database-guided mutagenesis (Desjarlais & Berg 1992 Proc Natl. Acad. Sci. USA 89, 7345–7349; Desjarlais & Berg 1993 Proc. Natl. Acad. Sci. USA 90, 2256–2260).

Combinatorial use of the coded contacts. The individual base contacts listed in Table 2, though part of a code, may not always result in sequence specific binding to the expected base triplet when used in any combination. In the first instance one must be aware of the possibility that zinc fingers may not be able to recognise certain combinations of bases in some triplets by use of this code, or even at all. Otherwise, the majority of inconsistencies may be accounted for by considering variations in the inclination of the trident reading head of a zinc finger with respect to the triplet with which it is interacting It appears that the identity of an amino acid at any one α-helical position is attuned to the identity of the residues at the other two positions to allow three base contacts to occur simultaneously. Therefore, for example, in order that Ala may pick out T in the triplet GTG, Arg must not be used to recognise G from position +6, since this would distance the former too far from the DNA (see for example the finger containing the amino acid sequence RGDALTSHER). (Seq ID No. 100). Secondly, since the pitch of the α-helix is 3.6 amino acids per turn, positions −1, +3 and +6 are not an integral number of turns apart, so that position +3 is nearer to the DNA than are −1 or +6. Hence, for example, short amino acids such as His and Asn, rather than the longer Arg and Gln, are used for the recognition of purines in the middle position of a triplet.

As a consequence of these distance effects one might say that the code is not really "alphabetic" (always identical amino acid:base contact) but rather "syllabic" (use of a small repertoire of amino acid:base contacts). An alphabetic code would involve only four rules, but syllabicity adds an additional level of complexity, since systematic combinations of rules comprise the code. Nevertheless, the recognition of each triplet is still best described by a code of syllables, rather than a catalogue of "logograms" (idiosyncratic amino acid:base contact depending on triplet).

Conclusions. The "syllabic" code of interactions with DNA is made possible by the versatile framework of the zinc finger: this allows an adaptability at the interface with DNA by slight changes of orientation, which in turn maintains a stoichiometry of one coplanar amino acid per base-pair in many different complexes. Given this mode of interaction between amino acids and bases it is to be expected that recognition of G and A by Arg and Asn/Gln respectively are important features of the code; but remarkably other interactions can be more discriminatory than was anticipated (Seeman et al., 1976). Conversely, it is clear that degeneracy can be programmed in the zinc fingers in varying degrees allowing for intricate interactions with different regulatory DNA sequences (Harrison & Travers, 1990; Christy & Nathans, 1989). One can see how this principle makes possible the regulation of differential gene expression by a limited set of transcription factors.

As already noted above, the versatility of the finger motif will likely allow other modes of binding to DNA. Similarly, one must take into account the malleability of nucleic acids such as is observed in Fairall et al., where a deformation of the double helix at a flexible base step allows a direct contact from Ser at position +2 of finger 1 to a T at the 3' position of the cognate triplet. Even in our selections there are instances of fingers whose binding mode is obscure, and may require structural analyses for clarification. Thus, water may be seen to play an important role, for example where short side chains such as Asp, Asn or Ser interact with bases from position −1 (Qian et al., 1993 J. Am. Chem. Soc. 115, 1189–1190; Shakked et al., 1994 Nature (London) 368, 469–478).

Eventually, it might be possible to develop a number of codes describing zinc finger binding to DNA, which could predict the binding site preferences of some zinc fingers from their amino acid sequence. The functional amino acids selected at positions −1, +3 and to an extent +6 in this study, are very frequently observed at the same positions in naturally occurring fingers (e.g. see FIG. 4. of Desjarlais and Berg 1992 Proteins 12, 101–104) supporting the existence of coded contacts from these three positions. However, the lack of definitive predictive methods is not a serious practical limitation as current laboratory techniques (here and in Thiesen & Bach 1990 and Pollock & Treisman 1990) will allow the identification of binding sites for a given DNA-binding protein. Rather, one can apply phage selection and a knowledge of the recognition rules to the converse problem, namely the design of proteins to bind predetermined DNA sites.

Prospects for the design of DNA-binding proteins. The ability to manipulate the sequence specificity of zinc fingers implies that we are on the eve of designing DNA-binding proteins with desired specificity for applications in medicine and research (Desjarlais & Berg, 1993; Rebar & Pabo, 1994). This is possible because, by contrast to all other DNA-binding motifs, we can avail ourselves of the modular nature of the zinc finger, since DNA sites can be recognised by appropriate combinations of independently acting fingers linked in tandem.

The coded interactions of zinc fingers with DNA can be used to model the specificity of individual zinc fingers de novo, or more likely in conjunction with phage display selection of suitable candidates. In this way, according to requirements, one could modulate the affinity for a given binding site, or even engineer an appropriate degree of indiscrimination at particular base positions. Moreover, the additive effect of multiply repeated domains offers the opportunity to bind specifically and tightly to extended, and hence very rare, genomic loci. Thus zinc finger proteins might well be a good alternative to the use of antisense nucleic acids in suppressing or modifying the action of a given gene, whether normal or mutant. To this end, extra functions could be introduced to these DNA binding domains by appending suitable natural or synthetic effectors.

EXAMPLE 3

From the evidence presented in the preceding examples, the inventors propose that specific DNA-binding proteins comprising zinc fingers can be "made to measure". To demonstrate their potential the inventors have created a three finger polypeptide able to bind site-specifically to a unique 9 bp region of a BCR-ABL fusion oncogene and to discriminate it from the parent genomic sequences (Kurzrock et al., 1988 N. Engl. J. Med. 319, 990–998). Using transformed cells in culture as a model, it is shown that binding to the target oncogene in chromosomal DNA is possible, resulting in blockage of transcription. Consequently, murine cells made growth factor-independent by the action of the oncogene (Daley et al., 1988 Proc. Natl. Acad. Sci. U.S.A. 85, 9312–9316) are found to revert to factor dependence on transient transfection with a vector expressing the designed zinc finger polypeptide.

DNA-binding proteins designed to recognise specific DNA sequences could be incorporated in chimeric transcription factors, recombinases, nucleases etc. for a wide range of applications. The inventors have shown that zinc finger mini-domains can discriminate between closely related DNA triplets, and have proposed that they can be linked together to form domains for the specific recognition of longer DNA sequences. One interesting possibility for the use of such protein domains is to target selectively genetic differences in pathogens or transformed cells. Here one such application is described.

There exist a set of human leukaemias in which a reciprocal chromosomal translocation t(9;22) (q34;q11) result in a truncated chromosome 22, the Philadelphia chromosome (Ph1)5, encoding at the breakpoint a fusion of sequences from the c-ABL protooncogene (Bartram et al., 1983 Nature 306, 277–280) and the BCR gene (Groffen et al., 1984 Cell 36, 93–99). In chronic myelogenous leukaemia (CML), the breakpoints usually occur in the first intron of the c-ABL gene and in the breakpoint cluster region of the BCR gene (Shtivelnan et al., 1985 Nature 315, 550–554), and give rise to a $p210^{BCR\text{-}ABL}$ gene product (Konopka et al., 1984 Cell 37, 1035–1042). Alternatively, in acute lymphoblastic leukaemia (ALL), the breakpoints usually occur in the first introns of both BCR and c-ABL (Hermans et al., 1987 Cell 51, 33–40), and result in a $p190^{BCR\text{-}ABL}$ gene product (FIG. 6) (Kurzrock et al., 1987 Nature 325, 631–635).

FIG. 6 shows the nucleotide sequences (Seq ID No.s 9–11) of the fusion point between BCR and ABL sequences in p190 cDNA, and of the corresponding exon boundaries in the BCR and c-ABL genes. Exon sequences are written in capital letters while introns are given in lowercase. Line 1 shows $p190^{BCR\text{-}ABL}$ cDNA; line 2 the BCR genomic sequence at junction of exon 1 and intron 1; and line 3 the ABL genomic sequence at junction of intron 1 and exon 2 (Hermans et al 1987). The 9 bp sequence in the $p190^{BCR\text{-}ABL}$ cDNA used as a target is underlined, as are the homologous sequences in genomic BCR and c-ABL.

Facsimiles of these rearranged genes act as dominant transforming oncogenes in cell culture (Daley et al., 1988) and transgenic mice (Heisterkamp et al., 1990 Nature 344, 251–253). Like their genomic counterparts, the cDNAs bear a unique nucleotide sequence at the fusion point of the BCR and c-ABL genes, which can be recognised at the DNA level by a site-specific DNA-binding protein. The present inventors have designed such a protein to recognise the unique fusion site in the $p190^{BCR\text{-}ABL}$ c-DNA. This fusion is obviously distinct from the breakpoints in the spontaneous genomic translocations, which are thought to be variable among patients. Although the design of such peptides has implications for cancer research, the primary aim here is to prove the principle of protein design, and to assess the feasibility of in vivo binding to chromosomal DNA in available model systems.

A nine base-pair target sequence (GCA, GAA. GCC) for a three zinc finger peptide was chosen which spanned the fusion point of the $p190^{BCR\text{-}ABL}$ cDNA (Hermans et al., 1987). The three triplets forming this binding site were each used to screen a zinc finger phage library over three rounds as described above in example 1. The selected fingers were then analysed by binding site signatures to reveal their preferred triplet, and mutations to improve specificity were made to the finger selected for binding to GCA. A phage display mini-library of putative BCR-ABL-binding three-finger proteins was cloned in fd phage, comprising six possible combinations of the six selected or designed fingers (1A, 1B; 2A; 3A, 3B and 3C) linked in the appropriate order. These fingers are illustrated in FIG. 7 (Seq ID No.s 12–17). In FIG. 7 regions of secondary structure are underlined below the list, while residue positions are given above, relative to the first position of the α-helix (position 1). Zinc finger phages were selected from a library of 2.6×10⁶ variants, using three DNA binding sites each containing one of the triplets GCC, GAA or GCA. Binding site signatures (example 2) indicate that fingers 1A and 1B specify the triplet GCC, finger 2A specifies GAA, while the fingers selected using the triplet GCA all prefer binding to GCT. Amongst the latter is finger 3A, the specificity of which we believed, on the basis of recognition rules, could be changed by a point mutation. Finger 3B, based on the selected finger 3A, but in which Gln at helical position +2 was altered to Ala should be specific for GCA. Finger 3C is an alternative version of finger 3A, in which the recognition of C is mediated by Asp+3 rather than by Thr+3.

The mini library was screened once with an oligonucleotide containing the 9 base-pair BCR-ABL target sequence to select for tight binding clones over weak binders and background vector phage. Because the library was small, the inventors did not include competitor DNA sequences for homologous regions of the genomic BCR and c-ABL genes but instead checked the selected clones for their ability to discriminate. It was found that although all the selected clones were able to bind the BCR-ABL target sequence and to discriminate between this and the genomic-BCR sequence, only a subset could discnminate against the c-ABL sequence which, at the junction between intron 1 and exon 2, has an 8/9 base-pair homology to the BCR-ABL target sequence (Hermans et al., 1987). Sequencing of the discriminating clones revealed two types of selected peptide, one with the composition 1A-2A-3B and the other with 1B-2A-3B. Thus both peptides carried the third finger (3B) which was specifically designed against the triplet GCA but peptide 1A-2A-3B was able to bind to the BCR-ABL target sequence with higher affinity than was peptide 1B-2A-3B.

Figure 8:
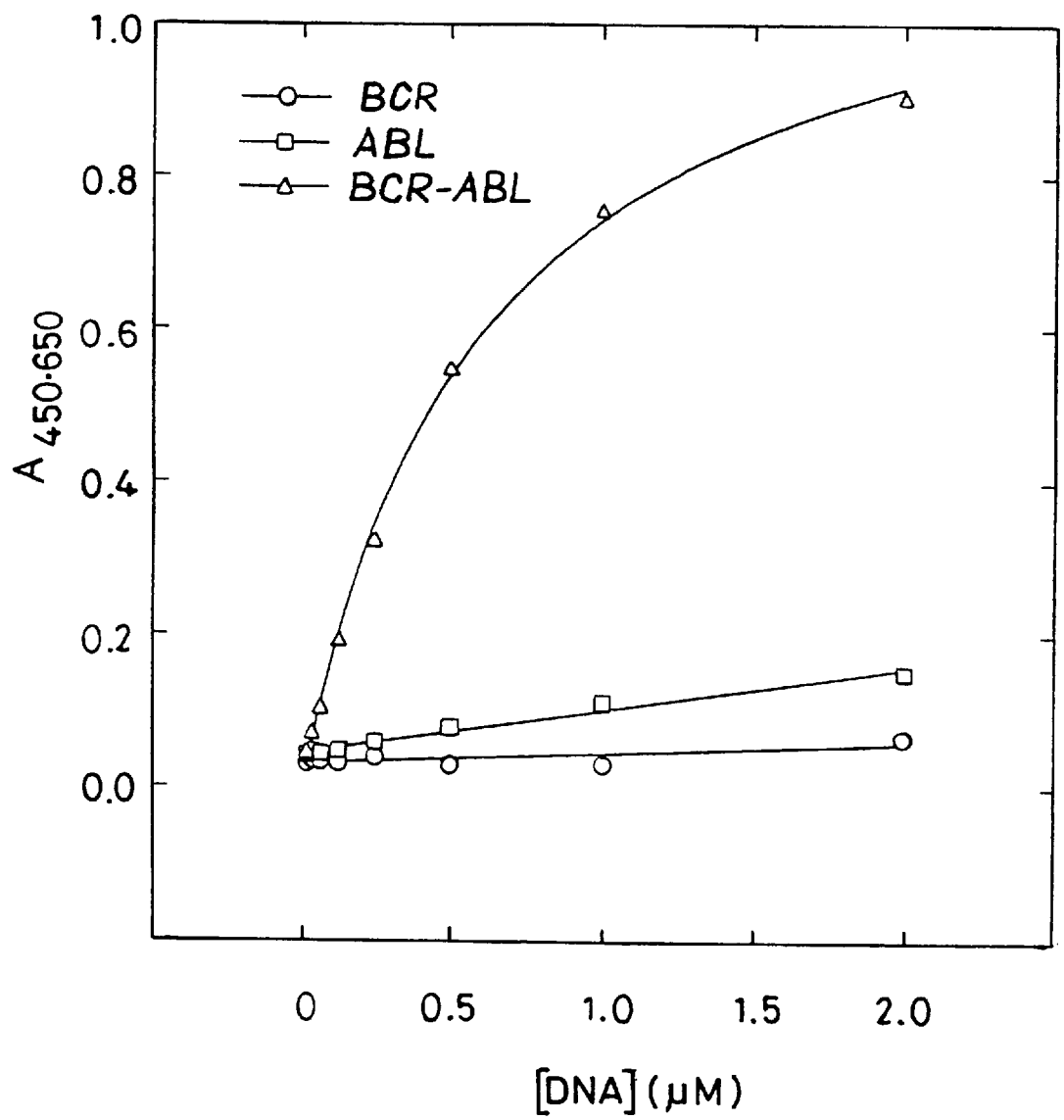
FIG. 8 is a graph of peptide binding (as measured by $A_{450-460}$ nm) against DNA concentration ($\mu$M) of target or control DNA sequences.

The peptide 1A-2A-3B, henceforth referred to as the anti-BCR-ABL peptide, was used in further experiments. The anti-BCR-ABL peptide has an apparent equilibrium dissociation constant ($K_d$) of 6.2+/–0.4×10$^{-7}$M for the p190$^{BCR-ABL}$ cDNA sequence in vitro, and discriminates against the similar sequences found in genomic BCR and c-ABL DNA, by factors greater than an order of magnitude (FIG. 8). Referring to FIG. 8, (which illustrates discrimination in the binding of the anti-BCR-ABL peptide to its p190$^{BCR-ABL}$ target site and to like regions of genomic BCR and c-ABL), the graph shows binding (measured as an $A_{450-650}$) at various [DNA]. Binding reactions and complex detection by enzyme immunoassay were performed as described previously, and a full curve analysis was used in calculations of the $K_d$ (Choo & Kiug 1993). The DNA used were oligonucleotides spanning 9bp either side of the fusion point in the cDNA or the exon boundaries. The anti-BCR-ABL peptide binds to its intended target site with a $K_d$=6.2+/–0.4×10$^{-7}$M, and is able to discriminate against genomic BCR and c-ABL sequences, though the latter differs by only one base pair in the bound 9 bp region. The measured dissociation constant is higher than that of three-finger peptides from naturally occurring proteins such as Spl (Kadonga et al., 1987 Cell 51, 1079–1090) or Zif268 (Christy et al., 1988), which have $K_d$s in the range of 10$^{-9}$M, but rather is comparable to that of the two fingers from the tramtrack (ttk) protein (Fairall et al., 1992). However, the affinity of the anti-BCR-ABL peptide could be refined, if desired, by site-directed mutations or by "affinity maturation" of a phage display library (Hawkins et al., 1992 J. Mol. Biol. 226, 889–896).

Figure 9:
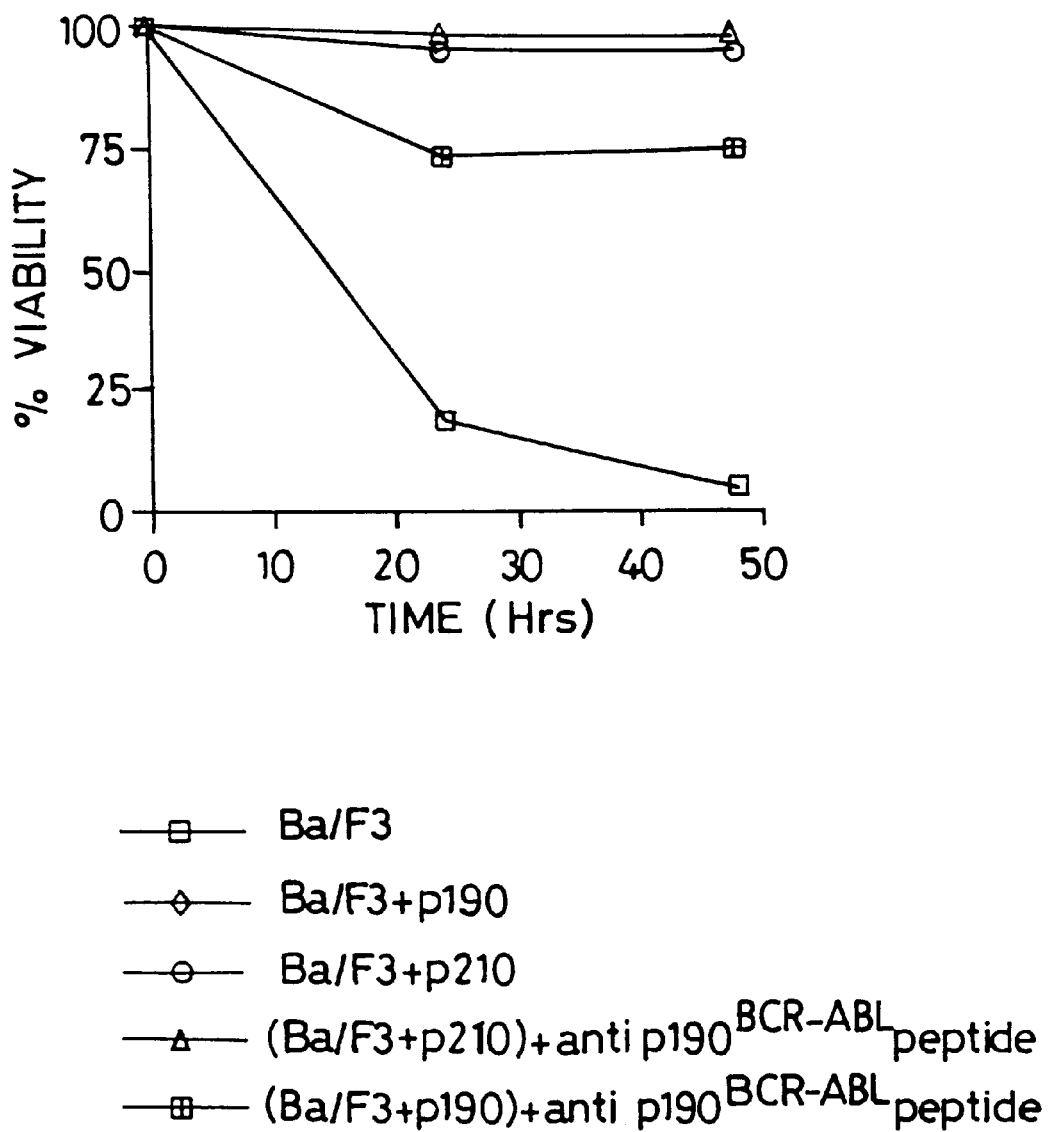
FIG. 9 is a graph showing percentage viability against time for various transfected cells.

Having established DNA discrimination in vitro, the inventors wished to test whether the anti-BCR-ABL peptide was capable of site-specific DNA-binding in vivo. The peptide was fused to the VP16 activation domain from herpes simplex virus (Fields 1993 Methods 5, 116–124) and used in transient transfection assays (FIG. 9) to drive production of a CAT (chloramphenicol acetyl transferase) reporter gene from a binding site upstream of the TATA box (Gorman et al., Mol. Cell. Biol. 2, 1044–1051). In detail the experiment was performed thus: reporter plasmids pMCAT6BA, pMCAT6A, and pMCAT6B, were constructed by inserting 6 copies of the p190$^{BCR-ABL}$ target site (CGCAGAAGCC, SEQ ID No. 121), the c-ABL second exon-intron junction sequence (TCCAGAAGCC, Seq ID No. 122), or the BCR first exon-intron junction sequence (CGCAGGTGAG Seq ID No. 123) respectively, into pMCAT3 (Luscher et al., 1989 Genes Dev. 3, 1507–1517). The anti-BCR-ABL/VP16 expression vector was generated by inserting the in-frame fusion between the activation domain of herpes simplex virus VP16 (Fields 1993) and the Zn finger peptide in the pEF-BOS vector (Mizushima & Shigezaku 1990 Nucl. Acids Res. 18, 5322). C3H10T1/2 cells were transiently co-transfected with 10 mg of reporter plasmid and 10 mg of expression vector. RSVL (de Wet et al., 1987 Mol. Cell Biol. 7, 725–737), which contains the Rous sarcoma virus long terminal repeat linked to luciferase, was used as an internal control to normalise for differences in transfection efficiency. Cells were transfected by the calcium phosphate precipitation method and CAT assays performed as described (Sanchez-Garcia et al., 1993 EMBO J. 12, 4243–4250). Plasmid pGSEC, which has five consensus 17-mer GAL4-binding sites upstream from the minimal promoter of the adenovirus Elb TATA box, and pMlVP16 vector, which encodes an in-frame fusion between the DNA-binding domain of GAL4 and the activation domain of herpes simplex virus VP16, were used as a positive control (Sadowski et al., 1992 Gene 118, 137–141).

C3H10T1/2 cells were transiently cotransfected with a CAT reporter plasmid and an anti-BCR-ABL/VP16 expression vector (pZNlA).

A specific (thirty-fold) increase in CAT activity was observed in cells cotransfected with reporter plasmid bearing copies of the p190$^{BCR-ABL}$ cDNA target site, compared to a barely detectable increase in cells cotransfected with reporter plasmid bearing copies of either the BCR or c-ABL semihomologous sequences, indicating in vivo binding.

The selective stimulation of transcription indicates convincingly that highly site-specific DNA-binding can occur in vivo. However, while transient transfections assay binding to plasmid DNA, the true target site for this and most other DNA-binding proteins is in genomic DNA. This might well present significant problems, not least since this DNA is physically separated from the cytosol by the nuclear membrane, but also since it may be packaged within chromatin.

To study whether genomic targeting is possible, a construct was made in which the afiti-BCR-ABL peptide was flanked at the N-terminus with the nuclear localisation signal from the large T antigen of SV40 virus (Kalderon et al., 1984 Cell 499–509), and at the C-terminus with an 11 amino acid c-myc epitope tag recognisable by the 9E10 antibody (Evan et al., 1985 Mol. Cell. Biol. 5, 3610–3616). This construct was used to transiently transfect the IL-3-dependent murine cell line Ba/F3 (Palacios & Steinmetz 1985 Cell 41, 727–734), or alternatively Ba/F3 +p190 and Ba/F3+p210 cell lines previously made IL-3-independent by integrated plasmid constructs expressing either p190$^{BCR-ABL}$ or p210$^{BCR-ABL}$, respectively. Staining of the cells with the 9E10 antibody followed by a secondary fluorescent conjugate showed efficient nuclear localisation in those cells transfected with the anti-BCR-ABL peptide.

The experimental details were as follows: the anti-BCR-ABL expression vector was generated in the pEF-BOS vector (Mizushirna & Shigezaku 1990), including an 11 amino acid c-myc epitope tag (EQKLISEEDLN, Seq ID No. 124) at the carboxy-terminal end, recognizable by the 9E10 antibody (Evan et al., 1985) and the nuclear localization signal (PKKKRKV, Seq ID No. 125) of the large T antigen of SV40 virus (Kalderon et al., 1984) at the amino-terminal end. Three glycine residues were introduced downstream of the nuclear localization signal as a spacer, to ensure exposure of the nuclear leader from the folded molecule. Ba/F3 cells were transfected with 25 mg of the anti-BCR-ABL expression construct tagged with the 9E10 c-myc epitope as described (Sanchez-Garcia & Rabbitts 1994 Proc. Natl. Acad. Sci. U.S.A. in press) and protein production analyzed 48 h later by immunofluorescence-labelling as follows. Cells were fixed in 4% (w/v) paraformaldehyde for 15 min, washed in phosphate-buffered saline (PBS), and permeabilized in methanol for 2 min. After blocking in 10% fetal calf serum in PBS for 30 min, the mouse 9E10 antibody was added. After a 30 min incubation at room temperature a fluorescein isothiocyanate (FITC)-conjugated goat anti-mouse IgG (SIGMA) was added and incubated for a further 30 min. Fluorescent cells were visualized using a confocal scanning microscope (magnification, 200x). Immunofluorescence of Ba/F3+p190 and Ba/F3+p210 cells transiently transfected with the anti-bcr-abl expression vector and stained with the 9E10 antibody was done. Expression and nuclear localisation of the anti-BCR-ABL peptide was observed. In addition, transfected Ba/F3+p190 cells show chromatin condensation and nuclear fragmentation into small apoptotic bodies, but not either untransfected Ba/F3+p190 cells or transfected Ba/F3+p210 cells.

The efficiency of transient transfection, measured as the proportion of immunofluorescent cells in the population, was 15–20%. When IL-3 is withdrawn from tissue culture, a corresponding proportion of Ba/F3+p190 cells are found to have reverted to factor dependence and die, while Ba/F3+p210 cells are unaffected. The experimental details were as follows: cell lines Ba/F3, Ba/F3 +p190 and Ba/F3 +p210 were maintained in Dulbecco's modified Eagle's medium (DMEM) supplemented with 10% fetal bovine serum. In the case of Ba/F3 cell line 10% WEHI-3B-conditioned medium was included as a source of IL-3. After the transfection with the anti-BCR-ABL expression vector, cells ($5\times10^5$/ml) were washed twice in serum-free medium and cultured in DMEM medium with 10% fetal bovine serum without WEHI-3B-conditioned medium. Percentage viability was determined by trypan blue exclusion. Data are expressed as means of triplicate cultures. The results are shown in graphical form in FIG. 9.

Figure 12:
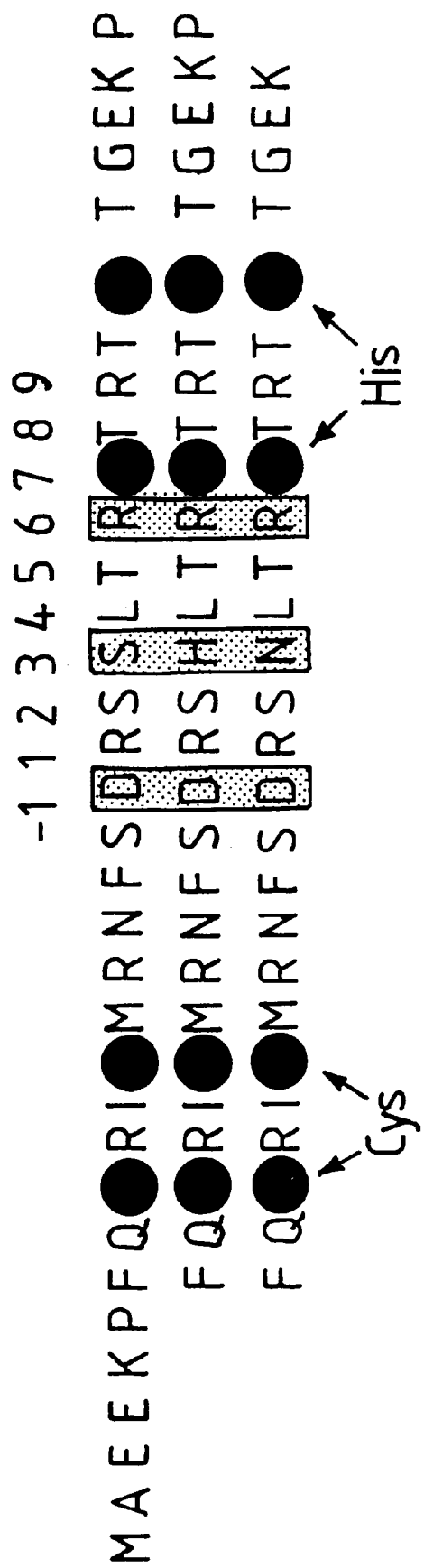
FIG. 12 shows the amino acid sequence of zinc fingers in a polypeptide (Seq ID No. 18) designed to bind to a particular DNA sequence (a ras oncogene).

Immunofluorescence microscopy of transfected Ba/F3+p190 cells in the absence of IL-3 shows chromatin condensation and nuclear fragmentation into small apoptotic bodies, while the nuclei of Ba/F3+p210 cells remain intact. Northern blots of total cytoplasmic RNA from Ba/F3 +p190 cells transiently transfected with the anti-BCR-ABL peptide revealed reduced levels of $p190^{BCR-ABL}$ mRNA relative to untransfected cells. By contrast, similarly transfected Ba/F3 +p210 cells showed no decrease in the levels of $p210^{BCR-ABL}$ mRNA (FIG. 12). The blots were performed as follows: 10 mg of total cytoplasmic RNA, from the cells indicated, was glyoxylated and fractionated in 1.4% agarose gels in 10 mM $NaPO_4$ buffer, pH 7.0. After electrophoresis the gel was blotted onto HYBOND-N (Amersham), UV-cross linked and hybridized to an $^{32}P$-labelled c-ABL probe. Autoradiography was for 14 h at $-70°$ C. Loading was monitored by reprobing the filters with a mouse b-actin cDNA. Northern filter hybridisation analysis of Ba/F3+p190 and Ba/F3+p210 cell lines transfected with the anti-BCR-ABL expression vector was done. When transfected with the anti-BCR-ABL expression vector, a specific downregulation of $p190^{BCR-ABL}$ mRNA was seen in Ba/F3+p190 cells, while expression of $p210^{BCR-ABL}$ was unaffected in Ba/F3+p210 cells.

In summary, the inventors have demonstrated that a DNA-binding protein designed to recognise a specific DNA sequence in vitro, is active in vivo where, directed to the nucleus by an appended localisation signal, it can bind its target sequence in chromosomal DNA. This is found on otherwise actively transcribing DNA, so presumably binding of the peptide blocks the path of the polymerase, causing stalling or abortion. The use of a specific polypeptide in this case to target intragenic sequences is reminiscent of anti-sense oligonucleotide- or ribozyme- based approaches to inhibiting the expression of selected genes (Stein & Cheng 1993 Science 261, 1004–1012). Like antisense oligonucleotides, zinc finger DNA-binding proteins can be tailored against genes altered by chromosomal translocations, or point mutations, as well as to regulatory sequences within genes. Also, like oligonucleotides which can be designed to repress transcription by triple helix formation in homopurine-homopyrimidine promoters (Cooney et al., 1988 Science 245, 725–730) DNA-binding proteins can bind to various unique regions outside genes, but in contrast they can direct gene expression by both up- or down- regulating, the initiation of transcription when fused to activation (Seipel et al., 1992 EMBO J. 11, 4961–4968) or repression domains (Herschbach et al., 1994 Nature 370, 309–311). In any case, by acting directly on any DNA, and by allowing fusion to a variety of protein effectors, tailored site-specific DNA-binding proteins have the potential to control gene expression, and indeed to manipulate the genetic material itself, in medicine and research.

EXAMPLE 4

The phage display zinc finger library described in the preceding examples could be considered sub-optimal in a number of ways:
  i) the library was much smaller than the theoretical maximum size;
  ii) the flanking fingers both recognised GCG triplets (in certain cases creating nearly symmetrical binding sites for the three zinc fingers, which enables the peptide to bind to the 'bottom' strand of DNA, thus evading the register of interactions we wished to set);
  iii) Asp+2 of finger three ("Asp++2") was dominant over the interactions of finger two (position +6) with the 5' base of the middle triplet;
  iv) not all amino acids were represented in the randomised positions.

In order to overcome these problems a new three-finger library was created in which:
  a) the middle finger is fully randomised in only four positions (−1, +3 and +6) so that the library size is smaller and all codons are represented. The library was cloned in the pCANTAB5E phagemid vector from Pharmacia, which allows higher transformation frequencies than the phage.
  b) the first and third fingers recognise the triplets GAC and GCA, respectively, making for a highly asymmetric binding site. Recognition of the 3'A in the latter triplet by finger three is mediated by Gln-1/Ala+2, the significance of which is that the short Ala+2 should not make contacts to the DNA (in particular with the 5' base of the middle triplet), thus alleviating the problem noted at (iii) above.

EXAMPLE 5

The human ras gene is susceptible to a number of different mutations, which can convert it into an oncogene. A ras oncogene is found in a large number of human cancers. One particular mutation is known as the G12V mutation (i.e. the polypeptide encoded by the mutant gene contains a substitution from glycine to valine). Because ras oncogenes are so common in human cancers, they are extremely significant targets for potential therapeutic methods.

A three finger protein has been designed which can recognise the G12V mutant of ras. The protein was produced using rational design based on the known specificity rules. In outline, a zinc finger framework (from one of the fingers selected to bind GCC) was modified by point mutations in position +3 to yield fingers recognising two additional different triplets. The finger recognising GCC and the two derivatives were cloned in pCANTAB5E and expressed on the surface of phage.

Originally, the G12V-binding peptide "r-BP" was to be selected from a small library of related proteins. The reason a library was to be used is that while it was clear to us what 8/9 of the amino acid:base contacts should be, it was not clear whether the middle C of the GCC triplet should be recognised by +3 Asp, or Glu, or Ser, or Thr (see Table 2 above). Thus a three-finger peptide gene was assembled from 8 overlapping synthetic oligonucleotides which were annealed and ligated according to standard procedures and the ~300bp product purified from a 2% agarose gel. The gene for finger 1 contained a partial codon randomisation at position +3 which allowed for inclusion of each of the above amino acids (D, E, S & T) and also certain other residues which were in fact not predicted to be desirable (e.g. Asr). The synthetic oligonucleotides were designed to have SfiI and NotI overhangs when annealed. The ~300 bp fragment was ligated into SfiI/NotI -cut FdSN vector and the ligation mixture was electroporated into DH5α cells. Phage were produced from these as previously described and a selection step carried out using the G12V sequence (also as described) to eliminate phage without insert and those phage of the library which bound poorly.

Following selection, a number of separate clones were isolated and phage produced from these were screened by ELISA for binding to the G12V ras sequence and discrimination against the wild-type ras sequence. A number of clones were able to do this, and sequencing of phage DNA later revealed that these fell into two categories, one of which had the amino acid Asn at the +3 randomised position, and another which had two other undesirable mutations.

The appearance of Asn at position +3 is unexpected and most probably due to the fact that proteins with a cytosine-specific residue at position +3 bind to some *E. coli* DNA sequence so tightly that they are lethal. Thus phage display selection is not always guaranteed to produce the tightest-binding clone, since passage through bacteria is essential to the technique, and the selected proteins may be those which do not bind to the genome of this host if such binding is deleterious.

$K_d$ measurements show that the clone with Asn+3 nevertheless binds the mutant G12V sequence with a $K_d$ in the nM range and discriminates against the wild-type ras sequence. However it was predicted that Asn+3 should specify an adenine residue at the middle position, whereas the polypeptide we wished to make should specify a cytosine for oiptimal binding.

Thus we assembled a three-finger peptide with a Ser at position +3 of Finger 1 (as shown in FIG. 12), again for using synthetic oligos. This tine the gene was ligated to pCANTAB5E phagemid. Transformants were isolated in the *E. coli* ABLE-C strain (from Stratagene) and grown at 30° C., which strain under these conditions reduces the copy number of plasmids so as to make their toxic products less abundant in the cells.

The amino acid sequence (Seq ID No. 18) of the fingers is shown in FIG. 12. The numbers refer to the α-helical amno acid residues. The fingers (F1, F2 & F3) bind to the G12V mutant nucleotide sequence:

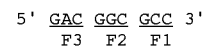

```
5'  GAC  GGC  GCC  3'
    F3   F2   F1
```

The bold A shows the single point mutation by which the G12V sequence differs from the wild type sequence.

Assay of the protein in eukaryotes (e.g. to drive CAT reporter production) requires the use of a weak oromoter. When expression of the anti-RAS (G12V) protein is strong, the peptide presumably binds to the wild-type ras allele (which is required) leading to cell death. For this reason, a regulatable promoter (e.g. for tetracycline) will be used to deliver the protein in therapeutic applications, so that the intracellular concentration of the protein exceeds the Kd for the G12V point mutated gene but not the Kd for the wild-type allele. Since the G12V mutation is a naturally occurring genomic mutation (not only a cDNA mutation as was the p190 bcr-abl) human cell lines and other animal models can be used in research.

In addition to repressing the expression of the gene, the protein can be used to diagnose the precise point mutation present in the genomic DNA, or more likely in PCR amplified genomic DNA, without sequencing. It should therefore be possible, without further inventive activity, to design diagnostic kits for detecting (e.g. point) mutations on DNA. ELISA-based methods should prove particularly suitable.

It is hoped to fuse the zinc finger binding polypeptide to an scFv fragment which binds to the human transferrin receptor, which should enhance delivery to and uptake by human cells. The transferrin receptor is thought particularly useful but, in theory, any receptor molecule (preferably of high affinity) expressed on the surface of a human target cell could act as a suitable ligand, either for a specific immunoglobulin or fragment, or for the receptor's natural ligand fused or coupled with the zinc finger polypeptide.

We claim:

1. A library of DNA sequences, each sequence encoding a zinc finger polypeptide for display on a viral particle, the zinc finger polypeptide comprising at least three zinc fingers, with one zinc finger having a partially randomized allocation of amino acids being positioned between two or more zinc fingers having a defined amino acid sequence, the partially randomized zinc finger having random allocation of amino acids at positions −1, +2, +3 and +6, position +1 being the first amino acid in the α-helix of the zing finger.

2. A library according to claim 1, wherein the partially randomized zinc finger further has random allocation of amino acids in at least one of the positions +1, +5 and +8.

3. A library according to claim 1 or 2, wherein the encoded partially randomized zinc finger is a zinc finger of the Zif268 polypeptide.

4. A library according to claim 1 as a fusion with the DNA encoding the minor cost protein of bacteriophage fd.

5. A method of designing a zinc finger polypeptide for binding to a particular target DNA sequence, comprising the steps of:
   comparing the binding to one or more DNA triplets of each of a plurality of zinc finger polypeptides having a partially randomized zinc finger positioned between two or more zinc fingers having defined amino acid sequence, the zinc finger polypeptides being encoded by a library in accordance with claim 1; and
   selecting those nucleic acid sequences encoding randomized zinc fingers which bind to the target DNA sequence.

6. A method of designing a zinc finger polypeptide for binding to a particular target DNA sequence, comprising the steps of:
   screening against at least a portion of the target DNA sequence a plurality of zinc finger polypeptides having a partially randomized zinc finger positioned between two or more zinc fingers having defined amino acid sequence, the portion of the target DNA sequence being sufficient to allow binding of some of the zinc finger polypeptides, the zinc finger polypeptides being encoded by a library in accordance with claim 1;
   comparing the binding to one or more DNA triplets of each of plurality zinc finger polypeptides having a partially randomized zinc finger positioned between two or more zinc fingers having defined amino acid sequence; and
   selecting those nucleic acid sequences encoding randomized zinc fingers which bind to the target DNA sequence.

7. A method of designing a zinc finger polypeptide for binding to a particular target DNA sequence, the method comprising the steps of:
- screening against at least a portion of the target DNA sequence a plurality of zinc finger polypeptides having a partially randomized zinc finger positioned between two or more zinc fingers having defined amino acid sequence, the portion of the target DNA sequence being sufficient to allow binding of some of the zinc finger polypeptides, the zinc finger polypeptides being encoded by a library in accordance with claim 1;
- comparing the binding to one or more DNA triplets of each of a plurality zinc finger polypeptides having a partially randomized zinc finger positioned between two or more zinc fingers having defined amino acid sequence;
- selecting certain of the screened randomized zinc fingers for analysis of preferred binding characteristics;
- and combining those sequences encoding desired zinc fingers to form a sequence encoding a zinc finger polypeptide which binds to the target DNA sequence.

8. A method for producing a zinc finger polypeptide for binding to a particular target DNA sequence, comprising the steps of:
- screening against at least a portion of the target DNA sequence a plurality of zinc finger polypeptides having a partially randomized zinc finger positioned between two or more zinc fingers having defined amino acid sequence, the portion of the target DNA sequence being sufficient to allow binding of some of the zinc finger polypeptides, the plurality of zinc finger polypeptides being coded by a library in according with claim 1;
- selecting those nucleic acid sequences encoding randomized zinc fingers which bind to the target DNA sequence; and
- expressing the selected nucleic acid sequences to produce zinc finger polypeptides which bind to the target DNA sequence.

9. A method of designing a zinc finger polypeptide for binding to a particular target DNA sequence, comprising the steps of:
- screening against at least a portion of the target DNA sequence a plurality of zinc finger polypeptides having a partially randomized zinc finger positioned between two or more zinc fingers having defined amino acid sequence, the portion of the target DNA sequence being sufficient to allow binding of some of the zinc finger polypeptides, the zinc finger polypeptides being encoded by a library in accordance with claim 1; and
- selecting those nucleic acid sequences encoding randomized zinc fingers which bind to the target DNA sequence.

10. A method according to claim 9, wherein two or more rounds of screening are performed.

11. A method of designing a zinc finger polypeptide for binding to a particular DNA target sequence, wherein a plurality of sequences encoding individual zinc fingers selected by the method of claim 9 are randomly combined in the appropriate order to encode a plurality of zinc finger polypeptides, the zinc finger polypeptides being screened against the target sequence, that combination of zinc finger sequences encoding a zinc finger polypeptide which binds to the target DNA sequence selected for use.

12. A method of modifying a nucleic acid sequence of interest present in a sample mixture by binding thereto a zinc finger polypeptide, wherein the zinc finger polypeptide is designed in accordance with claim 9, comprising contacting the sample mixture with zinc finger polypeptide having affinity for at least a portion of the sequence of interest, so as to allow the zinc finger polypeptide to bind specifically to the sequence of interest.

13. A method according to claim 12, further comprising the step of separating the zinc finger polypeptide (and nucleic acid sequences specifically bound thereto) from the rest of the sample.

14. A method according to claim 12, wherein the zinc finger polypeptide is bound to a solid phase support.

15. A method according to claim 12, wherein the presence of the zinc finger polypeptide bound to the sequence of interest is detected by the addition of one or more detection reagents.

16. A method according to claim 12, wherein the DNA sequence of interest is present in an acrylamide or agarose gel matrix, or is present on the surface of a membrane.

17. A DNA library according to claim 1, consisting of 64 sequences, each sequence comprising a different one of the 64 possible permutations of a DNA triplet, the library being arranged in twelve sub-libraries, wherein for any one sub-library one base in the triplet is defined and the other two bases are randomized.

18. A library according to claim 17 wherein the sequences are biotinylated.

19. A library according to claim 17, wherein the sequences are associated with separation means.

20. A library according to claim 19, wherein the separation means is selected from the group consisting of: a microtitre plate; magnetic or non-magnetic beads or particles capable of sedimentation; and an affinity chromatography column.

21. A kit for making a zinc finger polypeptide for binding to a DNA of interest, comprising:
- a library of DNA sequences, each sequence encoding a zinc finger polypedtide for display on a viral particle, the zinc finger polypeptide comprising at least three zinc fingers, with one zinc finger having a partially randomized allocation of amino acids being positioned between two or more zinc fingers having a defined amino acid sequence, the partially randomized zinc finger having random allocation of amino acids at positions −1, +2, +3 and +6. position +1 being the first amino acid in the α-helix of the zing finger;
- a vector molecule suitable for accepting one or more sequences from the library; and instructions for use.

22. A kit according to claim 21, wherein the vector directs the expression of the cloned sequences as a zinc finger polypeptide.

23. A kit according to claim 21, wherein the vector is capable of directing the expression of the cloned sequences as a zinc finger polypeptide displayed on the surface of a viral particle.

24. A kit according to claims 21 A library of DNA sequences, each sequence encoding a zinc finger polypeptide for display on a viral particle, the zinc finger polypeptide comprising at least three zinc fingers, with one zinc finger having a partially randomized allocation of amino acids being positioned between two or more zinc fingers having a defined amino acid sequence, the partially randomized zinc finger having random allocation of amino acids at positions −1, +2, +3 and +6, position +1 being the first amino acid in the α-helix of the zing finger, further comprising a library consisting of 64 sequences, each sequence comprising a different one of the 64 possible permutations of a DNA triplet, the library being arranged in twelve sub-libraries, wherein for any one sub-library one base in the triplet is defined and the other two bases are randomized.

25. A kit according to claim 24, further comprising appropriate buffer solutions and/or reagents for detection of bound zinc fingers.

26. A kit according to claim 25, further comprising a vector suitable for accepting one or more sequences selected from the library of DNA sequences encoding zinc fingers.

* * * * *

UNITED STATES PATENT AND TRADEMARK OFFICE
CERTIFICATE OF CORRECTION

PATENT NO.    : 6,013,453
DATED         : January 11, 2000
INVENTOR(S)   : Yen Choo, Aaron Klug and Isidro Sanchez Garcia It is certified that error appears in the above-identified patent and that said Letters Patent is hereby corrected as shown below:

Title page,
Item [73], correct the Assignee from "Medical Research Council, London, United Kingdom" to -- Gendaq Limited, London, England --.

Signed and Sealed this

Twenty-seventh Day of November, 2001

*Attest:*

*Attesting Officer*

NICHOLAS P. GODICI
*Acting Director of the United States Patent and Trademark Office*